(12) United States Patent
Vallejo et al.

(10) Patent No.: US 12,311,177 B2
(45) Date of Patent: *May 27, 2025

(54) METHOD AND APPARATUS FOR MULTI MODAL ELECTRICAL MODULATION OF PAIN USING COMPOSITE ELECTROMAGNETIC FIELDS

(71) Applicant: Medtronic SG, LLC, Minneapolis, MN (US)

(72) Inventors: Ricardo Vallejo, Bloomington, IL (US); David Leonardo Cedeno, Normal, IL (US); Nathan A. Torgerson, Andover, MN (US); Brian Andrew Smith, Minneapolis, MN (US)

(73) Assignee: Medtronic SG, LLC, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/300,305

(22) Filed: Jan. 22, 2020

(65) Prior Publication Data

US 2022/0088388 A1 Mar. 24, 2022
US 2025/0114603 A9 Apr. 10, 2025

(51) Int. Cl.
*A61N 1/36* (2006.01)
*A61N 1/05* (2006.01)

(52) U.S. Cl.
CPC ....... *A61N 1/36071* (2013.01); *A61N 1/0551* (2013.01); *A61N 1/36062* (2017.08); *A61N 1/36192* (2013.01); *A61N 1/36196* (2013.01)

(58) Field of Classification Search
CPC ............ A61N 1/36071; A61N 1/36062; A61N 1/0551; A61N 1/36192; A61N 1/36196
See application file for complete search history.

(56) References Cited

U.S. PATENT DOCUMENTS

| 2,622,601 A | 12/1952 | Nemec |
| 3,774,620 A | 11/1973 | Hansjurgens |
| 4,023,574 A | 5/1977 | Nemec |
| 4,071,033 A | 1/1978 | Nawracaj |
| 4,535,777 A | 8/1985 | Castel |
| 4,960,124 A | 10/1990 | Masaki |
| 5,224,477 A | 7/1993 | Itoh |
| 5,269,304 A | 12/1993 | Mattews |
| 5,324,317 A | 6/1994 | Reiss |

(Continued)

FOREIGN PATENT DOCUMENTS

| EP | 1011797 | 6/2000 |
| EP | 2630984 A1 | 8/2013 |

(Continued)

OTHER PUBLICATIONS

Response to Office Action dated Dec. 21, 2021, from counterpart Austrailian Application No. 2017312211 filed Mar. 14, 2022, 8 pp.

(Continued)

*Primary Examiner* — Lindsey G Wehrheim
(74) *Attorney, Agent, or Firm* — Shumaker & Sieffert, P.A.

(57) ABSTRACT

Apparatus and methods for managing pain uses a single composite modulation/stimulation signal with variable characteristics to achieve the same results as separate varying electromagnetic signals, including spinal cord stimulation or peripheral nerve stimulation.

22 Claims, 16 Drawing Sheets

(56) References Cited

U.S. PATENT DOCUMENTS

| | | |
|---|---|---|
| 5,683,422 A | 11/1997 | Rise |
| 5,716,377 A | 2/1998 | Rise et al. |
| 5,776,170 A | 7/1998 | MacDonald et al. |
| 5,791,344 A | 8/1998 | Schulman et al. |
| 5,833,709 A | 11/1998 | Rise et al. |
| 5,938,690 A | 8/1999 | Law et al. |
| 5,948,007 A | 9/1999 | Starkebaum et al. |
| 5,983,141 A | 11/1999 | Sluijter et al. |
| 6,002,964 A | 12/1999 | Feler et al. |
| 6,066,163 A | 5/2000 | John |
| 6,067,470 A | 5/2000 | Mower |
| 6,246,912 B1 | 6/2001 | Sluijter et al. |
| 6,366,813 B1 | 4/2002 | DiLorenzo |
| 6,393,325 B1 | 5/2002 | Mann et al. |
| 6,463,328 B1 | 10/2002 | John |
| 6,480,743 B1 | 11/2002 | Kirkpatrick et al. |
| 6,505,078 B1 | 1/2003 | King et al. |
| 6,539,263 B1 | 3/2003 | Schiff et al. |
| 6,584,358 B2 | 6/2003 | Carter et al. |
| 6,591,138 B1 | 7/2003 | Fischell et al. |
| 6,662,053 B2 | 12/2003 | Borkan |
| 6,665,562 B2 | 12/2003 | Gluckman et al. |
| 6,826,429 B2 | 11/2004 | Johnson et al. |
| 6,923,784 B2 | 8/2005 | Stein |
| 6,941,171 B2 | 9/2005 | Mann et al. |
| 7,149,574 B2 | 12/2006 | Yun et al. |
| 7,228,178 B2 | 6/2007 | Carroll et al. |
| 7,877,136 B1 | 1/2011 | Moffitt et al. |
| 8,209,021 B2 | 6/2012 | Alataris et al. |
| 8,359,102 B2 | 1/2013 | Alataris et al. |
| 8,364,273 B2 | 1/2013 | DeRidder |
| 8,380,316 B2 | 2/2013 | Hagedorn et al. |
| 8,380,318 B2 | 2/2013 | Kishawi et al. |
| 8,583,239 B2 | 11/2013 | Pless et al. |
| 8,738,154 B2 | 5/2014 | Zdeblick et al. |
| 8,774,927 B2 | 7/2014 | DeRidder |
| 8,788,044 B2 | 7/2014 | John |
| 8,977,363 B2 | 3/2015 | Carroll et al. |
| 8,977,373 B2 | 3/2015 | Felty et al. |
| 9,138,582 B2 | 9/2015 | Doan et al. |
| 9,175,053 B2 | 11/2015 | Zhu |
| 9,462,398 B2 | 10/2016 | DeRidder |
| 9,572,984 B2 | 2/2017 | Hou et al. |
| 9,895,539 B1 | 2/2018 | Heit et al. |
| 9,962,547 B2 | 5/2018 | Vallejo et al. |
| 10,039,930 B2 | 8/2018 | Vallejo et al. |
| 10,137,304 B2 | 11/2018 | Kallmyer |
| 10,188,864 B2 | 1/2019 | John |
| 10,434,311 B2 | 10/2019 | Vallejo et al. |
| 10,583,299 B2 | 3/2020 | John |
| 10,675,466 B2 | 6/2020 | Vallejo et al. |
| 10,850,102 B2 | 12/2020 | Vallejo et al. |
| 11,045,651 B2 | 6/2021 | Vallejo et al. |
| 11,090,490 B2 | 8/2021 | Vallejo et al. |
| 11,167,139 B2 * | 11/2021 | Vallejo ............... A61N 1/36196 |
| 11,918,811 B2 | 3/2024 | Vallejo et al. |
| 2002/0022866 A1 | 2/2002 | Borkan |
| 2002/0038137 A1 | 3/2002 | Stein |
| 2002/0072770 A1 | 6/2002 | Pless |
| 2002/0169485 A1 | 11/2002 | Pless et al. |
| 2003/0028072 A1 | 2/2003 | Fischell et al. |
| 2003/0078633 A1 | 4/2003 | Firlik et al. |
| 2003/0135248 A1 | 7/2003 | Stypulkowski |
| 2003/0149457 A1 | 8/2003 | Tcheng et al. |
| 2003/0204226 A1 | 10/2003 | Acosta et al. |
| 2004/0002635 A1 | 1/2004 | Hargrove et al. |
| 2004/0127953 A1 | 7/2004 | Kilgore et al. |
| 2004/0167584 A1 | 8/2004 | Carroll et al. |
| 2004/0172089 A1 | 9/2004 | Whitehurst et al. |
| 2004/0210270 A1 | 10/2004 | Erickson |
| 2004/0210271 A1 | 10/2004 | Campen et al. |
| 2004/0215286 A1 | 10/2004 | Stypulkowski |
| 2004/0267330 A1 | 12/2004 | Lee et al. |
| 2005/0021104 A1 | 1/2005 | DiLorenzo |
| 2005/0033381 A1 | 2/2005 | Carter et al. |
| 2005/0049649 A1 | 3/2005 | Luders et al. |
| 2005/0049651 A1 | 3/2005 | Whitehurst et al. |
| 2005/0065575 A1 | 3/2005 | Dobak |
| 2005/0081847 A1 | 4/2005 | Lee et al. |
| 2005/0149148 A1 | 7/2005 | King |
| 2005/0154425 A1 | 7/2005 | Boveja et al. |
| 2005/0171587 A1 | 8/2005 | Daglow et al. |
| 2005/0240242 A1 | 10/2005 | DiLorenzo |
| 2005/0245993 A1 | 11/2005 | Varrichio et al. |
| 2005/0246003 A1 | 11/2005 | Black et al. |
| 2006/0004422 A1 | 1/2006 | DeRidder |
| 2006/0009820 A1 | 1/2006 | Royle |
| 2006/0015153 A1 | 1/2006 | Gliner et al. |
| 2006/0074456 A1 | 4/2006 | Pyles et al. |
| 2006/0095088 A1 | 5/2006 | DeRidder |
| 2006/0100671 A1 | 5/2006 | Ridder |
| 2006/0116742 A1 | 6/2006 | DeRidder |
| 2006/0149337 A1 | 7/2006 | John |
| 2006/0184211 A1 | 8/2006 | Gaunt et al. |
| 2007/0027483 A1 | 2/2007 | Maschino et al. |
| 2007/0060954 A1 | 3/2007 | Cameron et al. |
| 2007/0073354 A1 | 3/2007 | Knudson et al. |
| 2007/0083240 A1 | 4/2007 | Peterson et al. |
| 2007/0150034 A1 | 6/2007 | Rooney et al. |
| 2007/0213771 A1 | 9/2007 | Spinner et al. |
| 2007/0265681 A1 | 11/2007 | Gerber et al. |
| 2009/0018617 A1 | 1/2009 | Skelton et al. |
| 2009/0024187 A1 | 1/2009 | Erickson et al. |
| 2010/0057178 A1 | 3/2010 | Simon |
| 2010/0249875 A1 | 9/2010 | Kishawi et al. |
| 2010/0274312 A1 | 10/2010 | Alataris et al. |
| 2011/0106208 A1 | 5/2011 | Faltys et al. |
| 2011/0184488 A1 | 7/2011 | DeRidder |
| 2011/0251229 A1 | 10/2011 | Watkins et al. |
| 2012/0016438 A1 | 1/2012 | Alataris et al. |
| 2012/0109020 A1 | 5/2012 | Wagner et al. |
| 2012/0197338 A1 | 8/2012 | Su et al. |
| 2012/0277621 A1 | 11/2012 | Gerber et al. |
| 2012/0277823 A1 | 11/2012 | Gerber et al. |
| 2012/0310140 A1 | 12/2012 | Kramer et al. |
| 2013/0035745 A1 | 2/2013 | Ahmed et al. |
| 2013/0211477 A1 | 8/2013 | Cullen et al. |
| 2013/0303828 A1 | 11/2013 | Hargrove |
| 2013/0304159 A1 | 11/2013 | Simon et al. |
| 2013/0325084 A1 | 12/2013 | Lee |
| 2014/0207203 A1 | 7/2014 | Ternes et al. |
| 2014/0257428 A1 | 9/2014 | Zhu |
| 2014/0277265 A1 | 9/2014 | Khalil et al. |
| 2015/0217117 A1 | 8/2015 | Hershey |
| 2016/0008604 A1 | 1/2016 | Doane et al. |
| 2016/0106985 A1 | 4/2016 | Zhu |
| 2016/0220813 A1 | 8/2016 | Edgerton et al. |
| 2016/0256689 A1 | 9/2016 | Vallejo et al. |
| 2016/0271413 A1 | 9/2016 | Vallejo et al. |
| 2018/0028812 A1 | 2/2018 | Vallejo et al. |
| 2018/0056073 A1 | 3/2018 | Torgerson |
| 2018/0243562 A1 | 8/2018 | Vallejo et al. |
| 2018/0243563 A1 | 8/2018 | Vallejo et al. |
| 2018/0250513 A1 | 9/2018 | Vallejo et al. |
| 2018/0353758 A1 | 12/2018 | Vallejo et al. |
| 2020/0164213 A1 | 5/2020 | John |
| 2020/0171308 A1 | 6/2020 | Vallejo et al. |
| 2021/0093865 A1 | 4/2021 | Vallejo et al. |
| 2021/0370067 A1 | 12/2021 | Vallejo et al. |
| 2022/0088388 A1 | 3/2022 | Vallejo et al. |

FOREIGN PATENT DOCUMENTS

| | | |
|---|---|---|
| EP | 2207587 B1 | 4/2015 |
| EP | 2853285 A1 | 4/2015 |
| EP | 3156099 B1 | 6/2018 |
| EP | 3500341 A1 | 6/2019 |
| WO | 1995019804 A1 | 7/1995 |
| WO | 9843700 A1 | 10/1998 |
| WO | 1998043700 A1 | 10/1998 |
| WO | 2004007018 A1 | 1/2004 |
| WO | 2006007048 A2 | 1/2006 |
| WO | 2006057734 A1 | 6/2006 |
| WO | 2007103324 A1 | 3/2007 |

(56) References Cited

FOREIGN PATENT DOCUMENTS

| WO | 2009061813 | A1 | 5/2009 |
|---|---|---|---|
| WO | 2009139968 | A2 | 11/2009 |
| WO | 2016154091 | A1 | 9/2016 |
| WO | 2018035521 | A1 | 2/2018 |

OTHER PUBLICATIONS

Communication pursuant to Article 94(3) EPC from counterpart European Application No. 17842263.0 dated Jul. 19, 2022, 6 pp.
Response to Examination Report dated Feb. 20, 2020, from Australian Patent Application No. 2017312211, filed Nov. 25, 2021, 16 pp.
Al-Kaisy et al., "Sustained Effectiveness of 10 kHz High-Frequency Spinal Cord Stimulation for Patients with Chronic, Low Back Pain: 24-Month Results of a Prospective Multicenter Study," Pain Medicine, vol. 15, No. 3, Mar. 1, 2014, pp. 347-354.
Al-Kaisy et al.; "10kHz High-Frequency Spinal Cord Stimulation for Chronic Axial Low Back Pain in Patients with No History of Spinal Surgery: A Preliminary, Prospective, Open Label and Proof-of-Concept Study," Neuromodulation: Technology at the Neural Interface, vol. 20, No. 1, Oct. 18, 2016, pp. 63-70.
Barr et al., "Electrophysiological interaction through the interstitial space between adjacent unmyelinated parallel fibers," Biophysical Journal, vol. 61, No. 5, May 1992, pp. 1164-1175.
Basser et al., "New currents in electrical stimulation of excitable tissues," Annual Review of Biomedical Engineering, vol. 2, No. 1, Aug. 2000, pp. 377-397.
Bawin et al., "Effects of modulated very high frequency fields on specific brain rhythms in cats," Brain Research, Vo. 58, No. 2, Aug. 30, 1973, pp. 365-384.
Benabid et al., "Therapeutic electrical stimulation of the central nervous system," Comptes Rendus Biologies, Vo. 328, No. 2, Feb. 2005, pp. 177-186.
Benyamin et al., "A Case of Spinal Cord Stimulation in Raynaud's Phenomenon: Can Subthreshold Sensory Stimulation Have an Effect? ," Pain Physician, vol. 10, May 2007, pp. 473-478.
Boston Scientific; "Precision Spinal Cord Stimulator System Clinical Manual"; Boston Scientific: Advancing science for life, 91083273-01 Rev A, 2015, pp. 1-74, Retrieved from the Internet: URL: https://www.uhms.org/images/MEDFAQs/9108327301_RevA_Precision_Spinal_Cord_Stimulator_System_Clinician_Manua.pdf. (Applicant points out, in accordance with MPEP 609.04(a), that the year of publication, 2005, is sufficiently earlier than the effective U.S. filing date, so that the particular month of publication is not in issue).
Brasil-Neto et al., "Experimental Therapy Of Epilepsy With Transcranial Magnetic Stimulation Lack Of Additional Benefit With Prolonged Treatment," Arquivos de neuro-psiquiatria, vol. 62, No. 1, Mar. 2004, pp. 21-25.
Bruet et al., "High frequency stimulation of the subthalamic nucleus increases the extracellular contents of striatal dopamine in normal and partially dopaminergic denervated rats," Journal of Neuropathology and Experimental Neurology, vol. 60, No. 01, Jan. 2001, pp. 15-24.
Bruet et al., "Neurochemical Mechanisms Induced By High Frequency Stimulation Of The Subthalamic Nucleus: Increase Of Extracellular Striatal Glutamate And GABA In Normal And Hemiparkinsonian Rats," Journal of Neuropathology and Experimental Neurology, vol. 62, No. 12, Dec. 2003, pp. 1228-1240.
Butt et al., "Histological Findings Using Novel Stimulation Parameters in a Caprine Model," Ref. F702 from Poster Session: European Journal of Pain Supplements, vol. 5, 2011, pp. 188-189. (Applicant points out, in accordance with MPEP 609.04(a), that the year of publication, 2011, is sufficiently earlier than the effective U.S. filing date, so that the particular month of publication is not in issue.).
Cemazar et al., "Electrochemotherapy of tumours resistant to cisplatin: a study in a murine tumour model," European Journal of Cancer 37, Feb. 2001, pp. 1166-1772.
Chakravarthy et al., "Mechanism of Action in Burst Spinal Cord Stimulation: Review and Recent Advances," Pain Medicine, vol. 20, Supplement 1, Jun. 2019, pp. S13-S22.
Ciria et al., "Antitumor effectiveness of different amounts of electrical charge in Ehrlich and fibrosarcoma Sa-37 tumors," BMC Cancer, BioMed Central, vol. 4, No. 87, Nov. 26, 2004, 10 pp.
Collins English Dictionary, definition of "in place of", accessed May 19, 2020, 1 pp., URL: https://www.collinsdictionary.com/dictionary/english/in-place-of.
Crapanzano et al., "High Frequency Spinal Cord Stimulation for Complex Regional Pain Syndrome: A Case Report," Pain Physician, vol. 19, Jan. 2017, pp. E177-E182.
Cucullo et al., "Very low intensity alternating current decreases cell proliferation," Glia, vol. 51, No. 1, Mar. 18, 2005, pp. 65-72.
D'Arcangelo et al., "Repetitive low-frequency stimulation reduces epileptiform synchronization in limbic neuronal networks," Neurobiology of Disease, vol. 19, No. 1-2, Jun. 2004, pp. 119-128.
DeLeo et al., "The tetrapartite synapse: Path to CNS sensitization and chronic pain," PAIN, vol. 122, No. 1, Feb. 21, 2006, pp. 17-21.
Deurloo et al., "The effect of subthreshold prepulses on the recruitment order in a nerve trunk analyzed in a simple and a realistic volume conductor model," Biological Cybernetics, vol. 85, No. 4, Feb. 9, 2001, pp. 281-291.
Dinner, "Effect of sleep on epilepsy," Journal of Clinical Neurophysiology, vol. 19, No. 6, Dec. 2002, pp. 504-513.
Eddicks et al., "Thoracic Spinal Cord Stimulation Improves Functional Status and Relieves Symptoms in Patients with Refractory Angina Pectoris: the first placebo-controlled randomised study," Heart, vol. 93, No. 5, Jan. 2007, pp. 585-590.
Faurie et al., "Effect of electric field vectoriality on electrically mediated gene delivery in mammalian cells," Biochimica et Biophysica Acta (BBA)—Biomembranes, vol. 1665, No. 1-2, Oct. 2004, pp. 92-100.
First Examination Report from counterpart Australian Application No. 2017312211, dated Sep. 21, 2021, 3 pp.
Gerloff et al., "Inhibitory influence of the ipsilateral motor cortex on responses to stimulation of the human cortex and pyramidal tract," Journal of Physiology, vol. 510, No. 1, Mar. 10, 1998, pp. 249-259.
Gerloff et al., "Stimulation over the human supplementary motor area interferes with the organization of future elements in complex motor sequences," Brian, vol. 120, No. 9, Oct. 1997, pp. 1587-1602.
Goodman et al., "Preemptive low-frequency stimulation decreases the incidence of amygdala-kindled seizures," Epilepsia, vol. 46, No. 1, Aug. 22, 2004, pp. 1-7.
Graham-Jones et al.., "Low-frequency septal stimulation increases tyrosine hydroxylase activity in the hippocampus," Pharmacology Biochemistry and Behavior, vol. 23, No. 4, Apr. 3, 1984, pp. 489-493.
Gravius et al., "Selective L4 Dorsal Root Ganglion Stimulation Evokes Pain Relief and Changes of Inflammatory Markers: Part I Profiling of Saliva and Serum Molecular Patterns," Neuromodulation: Technology at the Neural Interface, vol. 22, Aug. 15, 2018, pp. 44-52.
Gray et al., "Resistance to extinction after partial reinforcement training with blocking of the hippocampal theta rhythm by septal stimulation," Physiology and Behavior, vol. 8, No. 3, Mar. 1972, pp. 497-502.
Guthrie et al., "ATP Released from Astrocytes Mediates Glial Calcium Waves," The Journal of Neuroscience, vol. 19, No. 2, Jan. 15, 1999, pp. 520-528.
Hoekema et al., "Multigrid solution of the potential field in modeling electrical nerve stimulation," Computers and Biomedical Research, vol. 31, No. 5, Oct. 1998, pp. 348-362.
Holsheimer et al., "Clinical evaluation of paresthesia steering with a new system for spinal cord stimulation," Neurosurgery, vol. 42, No. 3, Mar. 1998, pp. 541-549.
Holsheimer et al., "Contact combinations in epidural spinal cord stimulation. A comparison by computer modeling," Stereotactic and Functional Neurosurgery, vol. 56, No. 4, 1991, Published online Jan. 31, 1992, pp. 220-233.
Holsheimer et al., "Effect of anode-cathode configuration on paresthesia coverage in spinal cord stimulation," Neurosurgery, vol. 43, No. 3, Sep. 1997, pp. 654-660.

(56) References Cited

OTHER PUBLICATIONS

Holsheimer et al., "Effects of electrode geometry and combination on nerve fibre selectivity in spinal cord stimulation," Medical and Biological Engineering and Computing, vol. 33, No. 5, Sep. 1995, pp. 676-682.

Holsheimer et al., "How do geometric factors influence epidural spinal cord stimulation? A quantitative analysis by computer modeling," Stereotactic and Functional Neurosurgery, vol. 56, No. 4, 1991, Published online Jan. 31, 1992, pp. 234-249.

Holsheimer et al., "Optimum electrode geometry for spinal cord stimulation: the narrow bipole and tripole," Medical and Biological Engineering and Computing, vol. 35, No. 5, Sep. 1997, pp. 493-497.

Holt et al., "Proactive behavioral effects of theta-blocking septal stimulation in the rat," Behavioral and Neural Biology, vol. 39, No. 1, Sep. 1983, pp. 7-21.

Holt et al., "Proactive behavioral effects of theta-driving septal stimulation on conditioned suppression and punishment in the rat," Behavioral Neuroscience, vol. 99, No. 1, Feb. 1985, pp. 60-74.

Irnich, "Paradigm shift in lead design," Pacing and Clinical Electrophysiology, vol. 22, No. 9, Sep. 1999, pp. 1321-1332.

Iyer, et al., "Priming stimulation enhances the depressant effect of low-frequency repetitive transcranial magnetic stimulation," Journal of Neuroscience, vol. 23, No. 34, Nov. 26, 2003, pp. 10867-10872.

Jang et al., "High frequency electrical stimulation promotes expression of extracellular matrix proteins from human astrocytes," Molecular Biology Reports, vol. 46, No. 4, Jul. 2, 2019, pp. 4369-4375.

John et al., "An exploration of the functional relationship between electroencephalographic potentials and differential inhibition," Annals of the New York Academy of Sciences, vol. 92, No. 3, Jul. 1961, pp. 1160-1182.

Kapural et al., "Comparison of 10-kHz High-Frequency and Traditional Low-Frequency Spinal Cord Stimulation for the Treatment of Chronic Back and Leg Pain: 24-Month Results From a Multicenter, Randomized, Controlled Pivotal Trial," Neurosurgery, vol. 79, No. 5, Nov. 2016, pp. 667-677.

Kapural et al., "Novel 10-kHz High-frequency Therapy (HF10 Therapy) Is Superior to Traditional Low-frequency Spinal Cord Stimulation for the Treatment of Chronic Bank and Leg Pain," Anesthesiology, vol. 123, No. 4, Oct. 2015, pp. 851-860.

Katayama et al., "Deep brain and motor cortex stimulation for post-stroke movement disorders and post-stroke pain," Neurosurgical Re-Engineering of the Damaged Brain and Spinal Cord, Acta Neurochirurgica Supplements, vol. 87, Springer, Vienna, 2003, pp. 121-123. (Applicant points out, in accordance with MPEP 609.04(a), that the year of publication, 2003, is sufficiently earlier than the effective U.S. filing date, so teh particular month of publication is not an issue).

Kilgore et al., "Nerve Conduction Block Utilising High-Frequency Alternating Current," Medical and Biological Engineering and Computing, vol. 42, No. 3, May 2004, pp. 394-406.

Kilgore et al., "Reversible Nerve Conduction Block Using Kilohertz Frequency Alternating Current," Neuromodulation, vol. 17, No. 3, Apr. 2014, pp. 242-255.

Kim et al., "Uniformity of Current Density Under Stimulating Electrodes, Critical Reviews in Biomedical Engineering," Critical Reviews in Biomedical Engineering, vol. 17, No. 6, Jan. 1990, pp. 585-619.

Kinfe et al., "Burst Spinal Cord Stimulation Increases Peripheral Antineuroinflammatory Interleukin 10 Levels in Failed Back Surgery Syndrome Patients With Predominant Back Pain," Neuromodulation: Technology at the Neural Interface, vol. 20, No. 4, Jan. 3, 2017, pp. 322-330.

Kinoshita et al., "Electric stimulation on human cortex suppresses fast cortical activity and epileptic spikes," Epilepsia, vol. 45, No. 7, Jun. 28, 2004, pp. 787-791.

Kinoshita et al., "Low-frequency repetitive transcranial magnetic stimulation for seizure suppression in patients with extratemporal lobe epilepsy—A pilot study," Seizure, vol. 14, No. 6, Sep. 2005, pp. 387-392.

Kossoff et al., "Effect of an external responsive neurostimulator on seizures and electrographic discharges during subdural electrode monitoring," Epilepsia, vol. 45, No. 12, Dec. 2004, pp. 1560-1567.

Kovner et al., "Disruption of short-term visual memory by electrical stimulation of inferotemporal cortex in the monkey," Journal of Comparative and Physiological Psychology, vol. 81, No. 1, Oct. 1972, pp. 163-172.

Krnjevic et al., "Stimulation-evoked changes in extracellular K+ and Ca2+ in pyramidal layers of the rat's hippocampus," Canadian Journal of Physiology and Pharmacology, vol. 60, No. 12, Dec. 1982, pp. 1643-1657.

Kumar et al., "The effects of spinal cord stimulation in neuropathic pain are sustained: a 24-month follow-up of the prospective randomized controlled multicenter trial of the effectiveness of spinal cord stimulation," Neurosurgery, vol. 63, No. 4, Oct. 2008, pp. 762-770.

Kuncel et al., "Selection of stimulus parameters for deep brain stimulation," Clinical Neurophysiology, vol. 115, No. 11, Nov. 2004, pp. 2431-2441.

Lambru et al., "Safety and Efficacy of Cervical 10kHz Spinal Cord Stimulation in Chronic Refractory Primary Headaches: a Retrospective Case Series," The Journal of Headache and Pain, vol. 17, No. 1, Jul. 8, 2016, pp. 1-8.

Lempka et al., "Computational Analysis of Kilohertz Frequency Spinal Cord Stimulation for Chronic Pain Management," Anesthesiology, vol. 122, No. 6, Jun. 2015, pp. 1362-1376.

Lertmanorat et al., "A novel electrode array for diameter-dependent control of axonal excitability: a simulation study," IEEE, Transactions on Biomedical Engineering, vol. 51, No. 7, Jul. 2004, pp. 1242-1250.

Lertmanorat et al., "Extracellular voltage profile for reversing the recruitment order of peripheral nerve stimulation: a simulation study," Journal of Neural Engineering, vol. 1, Nov. 17, 2004, pp. 202-211.

Levy, "The Need for Mechanism-Based Medicine in Neuromodulation," Neuromodulation Technology at the Neural Interface, vol. 15, No. 4, Aug. 1, 2012, pp. 273-279.

Li et al., "CaBP1, a neuronal Ca2+ sensor protein, inhibits inositol trisphosphate receptors by clamping intersubunit interactions," Proceedings of the National Academy of Sciences, vol. 110, No. 21, May 21, 2013, pp. 8507-8512.

Li et al., "An update on reactive astrocytes in chronic Pain," Journal of Neuroinflammation, vol. 16, No. 1, Jul. 9, 2019, 13 pp.

Liu et al., "Modulation of Axonal Excitability by High-Frequency Biphasic Electrical Current," IEEE Transactions on Biomedical Engineering, vol. 56, No. 9, Sep. 1, 2009, pp. 2167-2176.

Macmillan Dictionary (online); definition of "in place of", accessed May 19, 2020, 5 pp. Retrieved from Internet: URL: https://www.macmillandictionary.com/dictionary/british/in-place-of.

Manola et al., "Modelling motor cortex stimulation for chronic pain control: electrical potential field, activating functions and responses of simple nerve fibre models," Medical and Biological Engineering and Computing, vol. 43, No. 3, May 2005, pp. 335-343.

Matsuda et al., "Epileptogenesis induced by alternate-site kindling in bilateral hippocampi," Epilepsia, vol. 44, No. 3, Mar. 2003, pp. 292-298.

McIntyre et al., "Cellular effects of deep brain stimulation: model-based analysis of activation and inhibition," Journal of Neurophysiology, vol. 91, No. 4, Dec. 2003, pp. 1457-1469.

McIntyre et al., "Electric field and stimulating influence generated by deep brain stimulation of the subthalamic nucleus," Clinical Neurophysiology, vol. 115, No. 3, Mar. 2004, pp. 589-595.

McIntyre et al., "Excitation of central nervous system neurons by nonuniform electric fields," biophysical Journal, vol. 76, No. 2, Feb. 1999, pp. 878-888.

McIntyre et al., "Extracellular stimulation of central neurons: influence of stimulus waveform and frequency on neuronal output," Journal of Neurophysiology, vol. 88, Jun. 2002, pp. 1592-1604.

McIntyre et al., "Finite element analysis of the current-density and electric field generated by metal microelectrodes," Annals of Biomedical Engineering, vol. 29, No. 3, Mar. 2001, pp. 227-235.

(56) References Cited

OTHER PUBLICATIONS

McIntyre et al., "Selective microstimulation of central nervous system neurons," Annals of Biomedical Engineering, vol. 28, No. 3, Jan. 2000, pp. 219-233.

Medgadget, Product Information for "Senza Omnia Stimulator for Chronic Pain, with Widest Frequency Range, FDA Approved," Medagadget, Neurosurgery Orthopedic Surgery Pain Management, Nov. 2019, 5 pp, Retrieved from the Internet on May 18, 2020, URL: https://www.medadget.com/2019/11/senze-omnia-stimulator-for-chronic-pain-with-widest-frequency-range-fda-approved.html.

Menkes et al., "Slow-frequency repetitive transcranial magnetic stimulation in a patient with focal cortical dysplasia," Epilepsia, vol. 41, No. 2, Sep. 10, 1999, pp. 240-242.

Mie et al., "Induction of neural differentiation by electrically stimulated gene expression of NeuroD2," Journal of Biotechnology, vol. 100, No. 3, Aug. 26, 2002, pp. 231-238.

Miklavcic et al., "The effect of high frequency electric pulses on muscle contractions and antitumor efficiency in vivo for a potential use in clinical electrochemotherapy," Bioelectrochemistry, vol. 65, No. 2, Dec. 10, 2004, pp. 121-128.

Miklavcic et al., "The importance of electric field distribution for effective in vivo electroporation of tissues," Biophysical Journal, vol. 74, No. 5, May 1998, pp. 2152-2158.

Milligan et al., "Pathological and protective roles of glia in chronic pain," Nature Reviews Neuroscience, vol. 10, No. 1, Jan. 2009, pp. 23-36.

Misawa et al., "Low-frequency transcranial magnetic stimulation for epilepsia partialis continua due to cortical dysplasia," Journal of the Neurological Sciences, vol. 234, No. 1-2, Mar. 8, 2005, pp. 37-39.

Miyoshi et al., "Proposal of a new method for narrowing and moving the stimulated region of cochlear implants: animal experiment and numerical analysis," IEEE Transactions on Biomedical Engineering, vol. 446, No. 4, Apr. 1999, pp. 451-460.

Moro et al., "The impact on Parkinson's disease of electrical parameter settings in STN stimulation," Neurology, vol. 59, No. 5, May 10, 2002, pp. 706-713.

Mutani et al., "Effect of low frequency caudate stimulation on the EEG of epileptic neocortex," Brain Research, vol. 14, No. 3, Aug. 1969, pp. 749-753.

Nakagawa et al., "Suppression of spontaneous epileptiform activity with applied currents," Brain Research, vol. 567, No. 2, Jul. 30, 1991, pp. 241-247.

Nakamura, "Two types of inhibitory effects upon brain stem reticular neurons by low frequency stimulation of raphe nucleus in the rat," Brain Research, vol. 93, No. 1, Feb. 1977, pp. 140-144.

Nashold et al., "Dorsal Column Stimulation for Control of Pain," Journal of Neurosurgery, vol. 36, No. 5, May 1972, pp. 590-597.

Neurosurgery Survival Guide, About page, 2016, downloaded Jul. 15, 2020, 4 pages, Retrieved from the Internet: URL: http://neurosurgerysurvivalguide.com.

Nevro, "HF10(TM) Therapy Fact Sheet," Sep. 5, 2015, Rev A, 4 pp., Retrieved from the Internet: URL: https://sals3.patientpop.com/assets/docs/28990.pdf+&cd=1&hl=en&ct=clnk&gl=US.

Oakley et al., "A New Spinal Cord Stimulation System Effectively Relieves Chronic, Intractable Pain: A Multicenter Prospective Clinical Study," Neuromodulation: Technology at the Neural Interface, vol. 10, No. 3, Jan. 2007, pp. 262-278.

Oakley, "Spinal Cord Stimulation in Axial Low Back Pain: Solving the Dilemma," Pain Medicine, vol. 7, Supplement 1, May 2006, pp. S58-S63.

Perruchoud et al., "Analgesic Efficacy of High-Frequency Spinal Cord Stimulation: A Randomized Double-Blind Placebo-Controlled Study"; Neuromodulation: Technology at the Neural Interface, vol. 16, No. 4, Dec. 21, 2012, pp. 363-369.

Plonsey et al., "Electric field stimulation of excitable tissue," IEEE Transactions on Biomedical Engineering, vol. 42, No. 4, Apr. 1995, pp. 329-336.

Plonsey et al., "Electric Field Stimulation of Excitable Tissue: Determining Condition when an Excitable Membrane Can Be Considered Linear and Steady-State," IEEE Engineering in Medicine and Biology, vol. 17, No. 5, Sep./Oct. 1998, pp. 130-137.

Porter et al., "Hippocampal Astrocytes In Situ Respond to Glutamate Released from Synaptic Terminals," The Journal of Neuroscience, vol. 16, No. 16, Aug. 15, 1996, pp. 5073-5081.

Puc et al., "Techniques of signal generation required for electropermeabilization. Survey of electropermeabilization devices," Bioelectrochemistry, vol. 64, No. 2, Apr. 8, 2004, pp. 113-124.

Pucihar et al., "The effect of pulse repetition frequency on the uptake into electropermeabilized cells in vitro with possible applications in electrochemotherapy," Bioelectrochemistry, vol. 57, Jun. 4, 2002, pp. 167-172.

Pumir et al., "Effect of an externally applied electric field on excitation propagation in the cardiac muscle," Chaos: An Interdisciplinary Journal of Nonlinear Science, vol. 4, No. 3, Jul. 15, 1994, pp. 547-555.

Rattay et al., "Effective electrode configuration for selective stimulation with inner eye prostheses," IEEE Transactions on Biomedical Engineering, vol. 51, No. 9, Sep. 2004, pp. 1659-1664.

Reddy et al., "Comparison of Conventional and Kilohertz Frequency Epidural Stimulation in Patients Undergoing Trialing for Spinal Cord Stimulation: Clinical Considerations," World Neurosurgery, vol. 88, Apr. 2016, pp. 586-591.

Robb et al., "Transcutaneous Electrical Nerve Stimulation vs. Transcutaneous Spinal Electroanalgesia for Chronic Pain Associated with Breast Cancer," Journal of Pain and Symptom Management, vol. 33, No. 4, Apr. 2007, pp. 410-419.

Roitbak et al., "Depolarization of cortical glial cells in Response to Electrical stimulation of the Cortical Surface," Neuroscience, vol. 6, No. 12, Dec. 1981, pp. 2529-2537.

Rossi et al., "Reduction of cortical myoclonus-related epileptic activity following slow-frequency rTMS. A case study" (2004) NeuroReport, vol. 15, No. 2, Oct. 6, 2003, pp. 293-296.

Santos-Anderson et al., "Stimulation of rat medial or sulcal prefrontal cortex during passive avoidance learning selectively influences retention performance" Brain Research, vol. 103, No. 2, Jul. 21, 1975, pp. 243-259.

Satkauskas et al., "Electrophoretic Component of Electric Pulses Determines the Efficacy of In Vivo DNA Electrotransfer," Human Gene Therapy, vol. 16, No. 10, Oct. 2005, pp. 1194-1201.

Sato et al., "Spinal cord stimulation reduces mechanical hyperalgesia and glial cell activation in animals with neuropathic pain," Anesthesia and Analgesia, vol. 118, No. 2, Feb. 2014, pp. 464-472.

Sato et al., "The effects of modulating stimulation parameters of spinal cord stimulation (SCS) and glial activity in animals with neuropathic pain," Journal of Pain, vol. 118, No. 2, Apr. 2011, published online Feb. 2014, pp. 464-472.

Scholz et al., "The neuropathic pain triad: neurons, immune cells and glia," Nature Neuroscience, vol. 10, No. 11, Nov. 2007, pp. 1361-1368.

Second Examination Report from counterpart Australian Application No. 2017312211 dated Dec. 22, 2021, 3 pp.

Sepulveda et al., "Finite element analysis of current pathways with implanted electrodes," Journal of Biomedical Engineering, vol. 5, No. 1, Jan. 1983, pp. 41-48.

Shetty et al., "The Successful Treatment of Post-Implantation Iatrogenic Neuropathic Pain With Target-Field Stimulation Using Existing Stimulating System," European Journal of Pain Supplements, vol. 5, Supplement 1, Sep. 2011, p. 188.

Simpson et al., "A Randomized, Double-Blind, Crossover Study of the Use of Transutaneous Spinal Electroanalgesia in Patients with Pain from Chronic Critical Limb Ischemia," Journal of Pain and Symptom Management, vol. 28, No. 5, Nov. 2004, pp. 511-516.

Skelton et al., "Low-frequency stimulation of the perforant path produces long-term potentiation in the dentate gyms of unanesthetized rats," Canadian Journal of Physiology and Pharmacology, vol. 61, No. 10, Dec. 21, 1982, pp. 1156-1161.

St. Jude Medical, Product Information, "Eon Mini Rechargeable IPG," 2008, 2 pages. Retrieved from the Internet: URL: https://pdf.medicalexpo.com/pdf/st-jude-medical/eon-mini-rechargeable-ipg/70886-94459.html (Applicant points out, in accordance with MPEP

(56) References Cited

OTHER PUBLICATIONS 609.04(a), that the year of publication, 2008, is sufficiently earlier than the effective U.S. filing date, so that the particular month of publication is not in issue).
Stephens et al., "RNA-seq of spinal cord from nerve-injured rats after spinal cord stimulation," Molecular Pain, vol. 14, Nov. 12, 2018, 13 pp.
Struijk et al., "Theoretical performance and clinical evaluation of transverse tripolar spinal cord stimulation," (1998) IEEE Transactions on Rehabilitation Engineering, vol. 6, No. 3, Sep. 1998, pp. 277-285.
Struijk et al., "Transverse tripolar spinal cord stimulation: theoretical performance of a dual channel system," Medical and Biological Engineering and Computing, vol. 34, No. 4, Oct. 26, 1995, pp. 273-279.
Susil et al., "Separation between virtual sources modifies the response of cardiac tissue to field stimulation," Journal of Cardiovascular Electrophysiology, vol. 10, No. 5, Feb. 1999, pp. 715-727.
Sweet et al., "Paresthesia-Free High-Density Spinal Cord Stimulation for Postlaminectomy Syndrome in a Prescreened Population: A Prospective Case Series," Neuromodulation: Technology at the Neural Interface, vol. 19, No. 3, Sep. 1, 2015, pp. 260-267.
Tai et al., "Simulation of Nerve Block by High-Frequency Sinusoidal Electrical Current Based on the Hodgkin-Huxley Model," IEEE Transactions on Neural Systems and Rehabilitation Engineering, vol. 13, No. 3, Sep. 2005, pp. 415-422.
Tan et al., "Intensity Modulation: A Novel Approach to Percept Control in Spinal Cord Stimulation," Neuromodulation: Technology at the Neural Interface, vol. 19, No. 3, Sep. 1, 2015, pp. 254-259.
Tawfik et al., "Deep Brain Stimulation Results in Local Glutamate and Adenosine Release: Investigation into the Role of Astrocytes," Neurosurgery, vol. 67, No. 2, Aug. 2010, pp. 367-375.
Tergau et al., "Low-frequency repetitive transcranial magnetic stimulation improves intractable epilepsy," The Lancet, vol. 353, Jun. 26, 1999, p. 2209.
Thompson et al., "A Double Blind Randomised Controlled Clinical Trial on the Effect of Transcutaneous Spinal Electroanalgesia (TSE) on Low Back Pain," European Journal of Pain, vol. 12, No. 3, Jul. 9, 2007, pp. 371-377.
Tiede et al., "Novel Spinal Cord Stimulation Parameters in Patients with Predominant Back Pain," Neuromodulation: Technology at the Neural Interface, vol. 16, No. 4, Jan. 3, 2013, pp. 370-375.
Tilley et al., "Spinal Cord Stimulation Modulates Gene Expression in the Spinal Cord of an Animal Model of Peripheral Nerve Injury," Regional Anesthesia and Pain Medicine, vol. 41, No. 6, Nov.-Dec. 2016, pp. 750-756.
Trenite et al., "The impact of subclinical epileptiform discharges on complex tasks and cognition: relevance for aircrew and air traffic controllers," Epilepsy & Behavior, vol. 6, No. 1, Feb. 2005, pp. 31-34.
U.S. Appl. No. 17/521,521, filed Nov. 8, 2021, naming inventors Vallejo et al.
Ueno et al., "Localized stimulation of neural tissues in the brain by means of paried configuration of time-varying magnetic fields," Journal of Applied Physics, vol. 64, No. 10, Nov. 15, 1988, pp. 5862-5864.
Vallejo et al., "The Role of Glia and the Immune System in the Development and Maintenance of Neuropathic Pain," Pain Practice, vol. 10, No. 3, Apr. 29, 2010, pp. 167-184.
Vallejo et al., "Effects of Phase Polarity and Charge Balance Spinal Cord Stimulation on Behavior and Gene Expression in a Rat Model of Neuropathic Pain," Neuromodulation: Technology at the Neural Interface, vol. 23, No. 1, Apr. 3, 2019, pp. 26-35.
Vallejo et al., "Genomics of the Effect of Spinal Cord Stimulation on an Animal Model of Neuropathic Pain," Neuromodulation: Technology at the Neural Interface, vol. 19, No. 6, May 11, 2016, pp. 576-586.
Van Buyten et al., "High-Frequency Spinal Cord Stimulation for the Treatment of Chronic Back Pain Patients: Results of a Prospective Multicenter European Clinical Study," Neuromodulation Technology at the Neural Interface, vol. 16, No. 1, Oct. 2012, pp. 59-66.
Vedam-Mai et al., "Deep brain stimulation and the role of astrocytes," Molecular Psychiatry vol. 17, No. 2, May 31, 2011, pp. 124-131.
Velisek et al., "Low-frequency stimulation of the kindling focus delays basolateral amygdala kindling in immature rats," Neuroscience Letters, vol. 326, No. 1, Feb. 18, 2002, pp. 61-63.
Velisek et al., "Lowering of extracellular pH suppresses low-Mg(2+)-induces seizures in combined entorhinal cortex-hippocampal slices," Experimental Brain Research, vol. 101. No. 1, Sep. 1994, pp. 44-52.
Weiss et al., "Quenching: inhibition of development and expression of amygdala kindled seizures with low frequency stimulation," Neuroreport, vol. 6, No. 16 Nov. 1995, pp. 2171-2176.
Wieraszko, "Amplification of evoked potentials recorded from mouse hippocampal slices by very low repetition rate pulsed magnetic fields," Bioelectromagnetics: Journal of the Bioelectromagnetics Society, The Society for Physical Regulation in Biology and Medicine, The European Bioelectromagnetics Association, vol. 25, No. 7, Oct. 2004, pp. 537-544.
Windels et al., "Influence of the frequency parameter on extracellular glutamate and gamma-aminobutyric acid in substantia nigra and globus pallidus during electrical stimulation of subthalamic nucleus in rats," Journal of Neuroscience Research, vol. 72, No. 2, Apr. 15, 2003, pp. 259-267.
Yamamoto et al., "New method of deep brain stimulation therapy with two electrodes implanted in parallel and side by side," Journal of Neurosurgery, vol. 95, No. 6, Dec. 2001, pp. 1075-1078.
Yearwood et al., "A prospective comparison of Spinal cord stimulation (SCS) Using Dorsal Column Stimulation (DCS), Intraspinal Nerve Root Stimulation (INRS), and varying pulse Width in the Treatment of Chronic Low Back Pain," Digital Abstract presented at CNS 56th Annual Meeting, Chicago 2006, Jul. 10, 2006, 7 pgs.
Zhang et al., "Neuronal calcium-binding proteins 1/2 localize to dorsal root ganglia and excitatory spinal neurons and are regulated by nerve injury," Proceedings of the National Academy of Sciences, vol. 111, No. 12, Mar. 25, 2014, pp. E1149-E1158.
Response to First Examination Report dated Sep. 21, 2021, from counterpart Australian Application No. 2017312211 filed Nov. 26, 2021, 21 pp.
Prosecution History from U.S. Appl. No. 17/154,627, now U.S. Pat. No. 11,167,139, dated Apr. 14, 2021 through Oct. 20, 2021, 33 pp.
U.S. Appl. No. 16/901,202, filed Jun. 15, 2020, naming inventor Michael John, Sasha.
U.S. Appl. No. 16/901,206, filed Jun. 15, 2020, naming inventor Michael John, Sasha.
U.S. Appl. No. 17/007,563, filed Aug. 31, 2020, naming inventor Michael John, Sasha.
U.S. Appl. No. 17/060,610, filed Oct. 1, 2020, naming inventor Michael John, Sasha.
U.S. Appl. No. 17/007,570, filed Aug. 31, 2020, naming inventor Michael John, Sasha.
Office Action from counterpart Canadian Application No. 3,034,371 dated Aug. 7, 2023, 3 pp.
Office Action from counterpart Canadian Application No. 3,034,371 dated Mar. 18, 2024, 3 pp.

* cited by examiner 5-8 and 13-16 = caudad signal 1-4 and 9-12 = caphalad signal 1 to 8 = tonic signal (cephalad)

9 to16 = priming signal (caudad)

METHOD AND APPARATUS FOR MULTI MODAL ELECTRICAL MODULATION OF PAIN USING COMPOSITE ELECTROMAGNETIC FIELDS

CROSS-REFERENCE TO RELATED APPLICATIONS

This application claims priority to, and benefit of, U.S. Provisional Application No. 62/377,139, filed Aug. 19, 2016, entitled "Method and Apparatus for Multimodal Electrical Modulation of Pain Using Composite Electromagnetic Fields."

Further, this application is a continuation-in-part of co-pending U.S. patent application Ser. No. 15/075,550, filed Mar. 21, 2016, and entitled "Method and Apparatus for Multimodal Electrical Modulation of Pain."

This application is also a continuation-in-part of co-pending U.S. patent application Ser. No. 15/075,565, filed Mar. 21, 2016, and entitled "Method and Apparatus for Multimodal Electrical Modulation of Pain."

This application is also a continuation-in-part of co-pending U.S. patent application Ser. No. 15/075,582, filed Mar. 21, 2016, and entitled "Method and Apparatus for Multimodal Electrical Modulation of Pain."

This application is also a continuation-in-part of co-pending U.S. patent application Ser. No. 15/681,985, filed Aug. 21, 2017, and entitled "Method and Apparatus for Multimodal Electrical Modulation of Pain." The contents of all of the applications listed above are incorporated herein by reference in their entirety for all purposes.

FIELD

This disclosure relates to systems and methods for providing multimodal stimulation of neural structures, and, more specifically, for managing pain with an electromagnetic signal having multiple components of characteristic parameters.

BACKGROUND OF THE INVENTION

The term Spinal Cord Stimulation (SCS) is used to describe an advanced management therapy for chronic pain in which a varying electric field is applied to the Dorsal section of the spinal Cord (DC) via an electrode array (or electrode arrays) implanted in the epidural space. Conventional SCS also called tonic, traditionally utilizes an electric field varying between 40-250 Hz that is directed to a targeted pain location by overlaying it with a perceived tingling sensation, known as paresthesia, created by the stimulating electric field. This therapy has been clinically utilized for about half a century. The principal mode of action is based on the Gate Control Theory formulated by Melzack and Wall, although a full understanding of the mechanism has yet to be elucidated. The concept behind tonic SCS is that the paresthesia induced by the applied varying electric field masks, or "closes the gates to", pain signals travelling to the brain, however, the relationship between frequency, waveform shape, amplitude and pulse width and the mechanism by which SCS provides an analgesic effect is not fully understood.

SUMMARY

Disclosed herein are apparatus and methods for managing pain in a patient by using multimodal stimulation of neural structures, with an electromagnetic signal having multiple components of characteristic frequencies, amplitudes, and phase polarities. Multimodal modulation for pain management, in accordance with the disclosure, contemplates the use of oscillating electromagnetic fields which is applied via an array of electrodes (referred as contacts or leads) to a particular neural structure using temporal and amplitude characteristics, to modulate glial and neuronal interactions as the mechanism for relieving chronic pain. More specifically, exemplary aspects provide an apparatus and method for modulating the expression of genes involved in diverse pathways including inflammatory/immune system mediators, ion channels and neurotransmitters, in both the Spinal Cord (SC) and Dorsal Root Ganglion (DRG). In one exemplary embodiment, such expression modulation is caused by spinal cord stimulation or peripheral nerve stimulation. In one embodiment, the amplitudes and frequencies of the signal or signals used to create the multimodal stimulation of neural structures may be optimized for improved pain relief and minimal power usage in an implantable multimodal signal generator, as described herein.

According to one exemplary aspect, the present disclosure provides an electromagnetic stimulation system comprising: memory for storing a plurality of multimodal signal parameter programs; a selection device for selecting one of the plurality of multimodal signal parameter programs, a signal generator controllable by a selected of the plurality of multimodal signal parameter programs; and an output unit for connection to at least one electrode; wherein the stimulation system is configured to provide a composite electric signal having a priming phase signal segment and a tonic phase signal segment to the at least one electrode via the output unit. In one embodiment, the system further comprises an enclosure of biocompatible material surrounding the multimodal signal generator and output unit. In another embodiment, the selection device is configured for receiving user definable instructions for modifying any of the respective amplitudes, relative phases, waveform shapes, and widths of the priming phase signal segment and the tonic phase signal segment of the composite electric signal. In another embodiment, the selection device is configured for receiving user definable instructions for modifying any of the amplitudes and frequency of the composite electric signal.

According to still another exemplary aspect, the present disclosure provides a method for managing pain in a subject comprises activating glial cells by regulating any of genes for calcium binding proteins, cytokines, cell adhesion or specific immune response proteins without the administration of a pharmacological compound to the subject. In one embodiment, activating the glial cells comprises exposing the glial cells to an electromagnetic stimulus comprising multiple signal phase components.

According to yet another exemplary aspect, the present disclosure provides a method for managing pain in a subject comprising: A) lowering a threshold for depolarization of nerve fibers in the subject with a component of the composite electromagnetic field; and B) simultaneously activating glial cells with a second component of the composite electromagnetic field; without the administration of a pharmacological compound to the subject. In one embodiment, the components of the composite electromagnetic field have any of different respective frequencies, amplitudes, phases or harmonic content. In another embodiment, the composite electromagnetic field may be provided either by a single electromagnetic signal or by the combination of two or more different electromagnetic signals.

According to still another exemplary aspect, a method for managing pain in a subject comprises: A) lowering a threshold for depolarization of nerve fibers in the subject with a first component of a composite electromagnetic field for a first period of time; and B) simultaneously modulating glial cell activity with a second component of a composite electromagnetic field during a second period of time not identical to the first period of time; wherein the composite electromagnetic field change synaptic plasticity of neurons and glial cells within the neural structures.

According to another exemplary aspect, the present disclosure provides a method for managing pain in a subject comprising: A) lowering a threshold for depolarization of nerve fibers in the subject with a first phase segment of a biphasic signal; and B) modulating glial cell activity in the subject with a second phase segment of the biphasic signal; wherein manipulation of the biphasic signal changes synaptic plasticity of neurons and glial cells within the nerve fibers.

According to still another exemplary aspect, the present disclosure provides a method for managing pain in a subject comprising: A) activating glial cells by multimodal electromagnetic stimulation regulating any of genes for calcium binding proteins, cytokines, cell adhesion or specific immune response proteins; and B) administering a pharmacological substance to the subject systemically, epidurally, or intrathecally during a time period. In one embodiment, such a pharmacological substance may be injected through the stimulation lead, which may have a port to deliver the pharmacological agent directly into the epidural or intrathecal space. Optionally, the pharmacological agent may be impregnated onto the stimulation lead using a slow release formulation in order to provide a slow elution of the pharmacological substance into the neural tissue around the lead.

According to yet another exemplary aspect, the present disclosure provides a method for managing pain in a subject comprising: A) lowering a threshold for depolarization of nerve fibers in the subject with a component of the composite electromagnetic field; and B) simultaneously modulating glial cell activity with other components of the composite electromagnetic field; wherein the components of the composite electromagnetic field control the balance of glutamate and glutamine in a calcium dependent manner within the modulated glial cells. In one embodiment, the components of the composite electromagnetic field have any of different respective frequencies, amplitudes, phases, harmonic content, or width for rectangular waveforms. In another embodiment, the components of the composite electromagnetic fields may be provided either by a single electrical signal or by more than one different electrical signals.

According to still another exemplary aspect, a method for managing pain in a subject comprises: A) modulating glial cells with an asymmetric biphasic electromagnetic signal having variable duration of the anodic phase thereof selected to modulate the amount of glutamate released therefrom; and B) modulating glial cells with an asymmetric biphasic electromagnetic signal having variable duration of the cathodic phase thereof selected to modulate the amount of glutamate released therefrom.

According to yet another aspect, a method for managing pain in a subject comprises: A) modulating glial cells with an asymmetric biphasic electromagnetic signal having variable duration of the cathodic and anodic phases thereof selected to modulate the amount of glutamate released therefrom, wherein the electromagnetic fields control the balance of glutamate and glutamine in a calcium dependent manner within the modulated glial cells.

Also disclosed herein is an apparatus comprising a signal generation module that is configured for electrically coupling with one or more leads.

Optionally, the signal generation module is arranged for generating a composite electric signal. The composite electric signal can be a summed signal of multiple electric signals. Optionally, the signal generation module is arranged for generating a multimodal signal, such as a frequency-modulated signal. The composite signal and/or the multimodal signal can be provided to the one or more leads.

Optionally, the signal generation module comprises at least a first and a second electric signal source or terminal and the one or more leads comprise at least a first and a second subgroup of electrodes. The first subgroup of electrodes can be electrically coupled to the first electric signal source and/or terminal and the second subgroup of electrodes can be electrically coupled to the second electric signal source and/or terminal.

Optionally, the signal generation module is configured for having an operating mode for providing at least first and second electric signals corresponding to the first and second electromagnetic stimulus as described herein. Optionally, the first and second electric signals have a different frequency, amplitude and phase polarity characteristics.

Optionally, the signal generation module is configured for having an operating mode for providing electric signals to the electrodes corresponding to the electromagnetic stimulus of any of the methods described herein.

Optionally, the signal generation module can be configured for having an operating mode for providing a first electric signal having a frequency to the first subgroup of electrodes, and a at least a second electric signal having the same frequency to the second subgroup of electrodes. The frequency can be between 500 Hz and 1,500 Hz. Other parameters of the first and second electric signals may be different, such as the pulse width and/or amplitude. The first electric signal can be fired synchronously, i.e., simultaneously, with the second electric field, or asynchronously, e.g., with a given time delay, relative to the first electric signal.

As used herein, a signal generation module that is configured for having an operating mode may comprise a memory module containing instructions defining at least an operating mode as described, wherein the operating mode is optionally a user-selectable operating mode and the memory module optionally comprises instructions for additional operating modes. In certain embodiments the signal generation module is configured for delivering electrical signals to one or more leads as specified.

Optionally, the signal generation module comprises two or more electric signal sources, such as signal generators, that are independently controllable, and are configured for delivering electric signals with parameters that can be set separately for each of the electric signal sources.

Optionally, the apparatus is a non-implantable, e.g., trialing, system, comprising a signal generation module comprising at least two signal generators configured for delivering electric signals with parameters that can be set separately for each of the signal generators, for example a Priming signal and a Tonic signal.

Optionally, an implantable multimodal generator is provided that is adapted for electrically coupling with one or more leads, or optionally is coupled with one or more leads. The implantable multimodal generator comprises generator circuitry and a housing. The housing can hermetically seal the generator circuitry and can be made of a durable biocompatible material. The generator has an output interface for establishing electrical connection with electrodes implemented in one or more leads, e.g., at least a first and second terminal for electrically coupling to a first and second subgroup of electrodes implemented on one or more leads.

Optionally the implantable multimodal generator comprises two or more signal generators and timer electronic circuitry that can slave one of the signal generators to another signal generator, such that a delay can be produced between signals generated from the at least two signal generators.

According to another exemplary aspect of the disclosure, an electromagnetic stimulation device is provided including an output unit for connection to at least one electrode, and a signal generator, wherein the stimulation device is arranged for providing a multimodal stimulation signal to the at least one electrode via the output unit. The multimodal stimulation signal can be an electromagnetic signal. At least one electrode is configured for exposing glial cells and neurons to the multimodal stimulation signal. At least one lead can include an array of electrodes, or a plurality of arrays of electrodes. The electromagnetic stimulation device can be a pain treatment device.

Optionally, the signal generator is arranged for generating a multimodal electric signal, such as a frequency modulated signal or an amplitude modulated signal. The multimodal electric signal can be provided to at least one lead.

Optionally, the electromagnetic stimulation device may have an output unit that includes a first output for connection to a first lead and a second output for connection to a second lead. The first lead can include a first array of electrodes. The second lead can include a second array of electrodes.

Optionally, the signal generator is arranged for providing a first electric signal to the first output and at least a second electric signal to at least a second output. The first electric signal and the other electric signals can differ in a parameter such as amplitude, frequency, phase, phase polarity, waveform shape, and width. The first electric signal and the other electric signals may correspond in a parameter such as amplitude, frequency, phase, phase polarity, waveform shape, and width. At least a second electric signal can be a tonic stimulation signal, and the first electric signal can have a frequency higher than the frequency of the tonic stimulation signal.

According to another exemplary aspect of the disclosure, a method for operating a signal generation module is provided. The method includes connecting the signal generation module to one or more leads. The leads can already have been provided to a body of a subject. The method includes generating, using the signal generation module, a first oscillating electromagnetic field at least one of the one or more leads and generating, using the signal generation module, a second oscillating electromagnetic field at least one of the one or more leads. The first oscillating electromagnetic field and at least one of the other oscillating electromagnetic fields can have at least one uncommon parameter there between.

According to another exemplary aspect of the disclosure, an electrically conducting material is provided, such as a metal or conductive polymer, e.g., in the form of an electrode, for use in administering an electromagnetic stimulus into a subject for the treatment of pain. The electromagnetic stimulus can include a first electromagnetic stimulus and at least a second electromagnetic stimulus. The first stimulus and the other stimuli may have at least one uncommon parameter there between. The various components of the composite signal can be made of individual electric signals, or the composite signal is generated as an individual electrical signal, as described herein.

Optionally, the first component of the composite signal is a Priming signal and a second component is a Tonic signal. The first component can have a frequency between 200 Hz to 100 kHz. The second component can have a frequency lower than the first stimulus, such as between 10 Hz and 500 Hz. In an exemplary embodiment, the frequency of the first stimulus and the frequency of the second stimulus has a ratio in the range of 2:1 to 40:1, 4:1 to 40:1, 10:1 to 40:1, 20:1 to 40:1, up to 70:1, up to 140:1, etc.

According to another exemplary aspect of the disclosure, an electromagnetic stimulation system comprises a memory for storing a plurality of multimodal signal parameter programs; a selection device for selecting one of the plurality of multimodal signal parameter programs; a multimodal signal generator controllable by a selected of the plurality of multimodal signal parameter programs; and an output unit for connection to at least one electrode; wherein the stimulation device is configured to provide a multimodal stimulation signal generated by the multimodal signal generator in accordance with a selected of the multimodal signal parameter programs to the at least one electrode via the output unit. The system may further comprise an enclosure of biocompatible material surrounding the multimodal signal generator and output unit. In one embodiment, the multimodal signal generator generates a first and a second electric signals in an operational mode thereof. In one embodiment, the system may be combined with at least one electrode comprising at least a first and a second subgroup of electrodes, and wherein the first subgroup of electrodes is electrically coupled to the first electric signal and the second subgroup of electrodes is electrically coupled to the second electric signal.

According to another exemplary aspect of the disclosure, optimization of the therapy comprises the methodical selection of multimodal stimulation waveforms and parameters that fits the needs of the patient treated. This may include a combination of components in a manner described herein. Multimodal stimulation may also be optimized by setting the most appropriate electromagnetic field that modulates neural structures by selecting monopolar, bipolar, or guarded cathode arrangements in vertebral levels or peripheral nerves that are associated with a particular anatomical region of the body in which the patient experiences pain.

According to another exemplary aspect of the disclosure, a method of managing pain in a subject comprises: lowering a threshold for depolarization of nerve fibers in the subject with a first phase segment of a biphasic signal; and modulating glial cell activity in the subject with a second phase segment of the biphasic signal.

In exemplary embodiments, a first phase segment of the biphasic signal is derived from a first electric signal having a current amplitude set to a value corresponding to a percentage of a Priming Perception Threshold (PPT) of the subject, and the second phase segment of the biphasic signal is derived from a second electric signal having a current amplitude set to a value corresponding to a percentage of a Tonic Perception threshold (TPT) of the subject. As used herein, the term Perception Threshold or Paresthesia Threshold (PT) relates to any type of stimulation, including priming and tonic stimulations.

It will be appreciated that any of the aspects, features and options described in view of the methods apply equally to the system, signal generation module and stimulation device. It will be understood that any one or more of the above aspects, features and options as described herein can be combined.

BRIEF DESCRIPTION THE DRAWINGS

The various features and advantages of the present invention may be more readily understood with reference to the following detailed description taken in conjunction with the accompanying drawings, wherein like reference numerals designate like structural elements, and in which.

Figure 18:
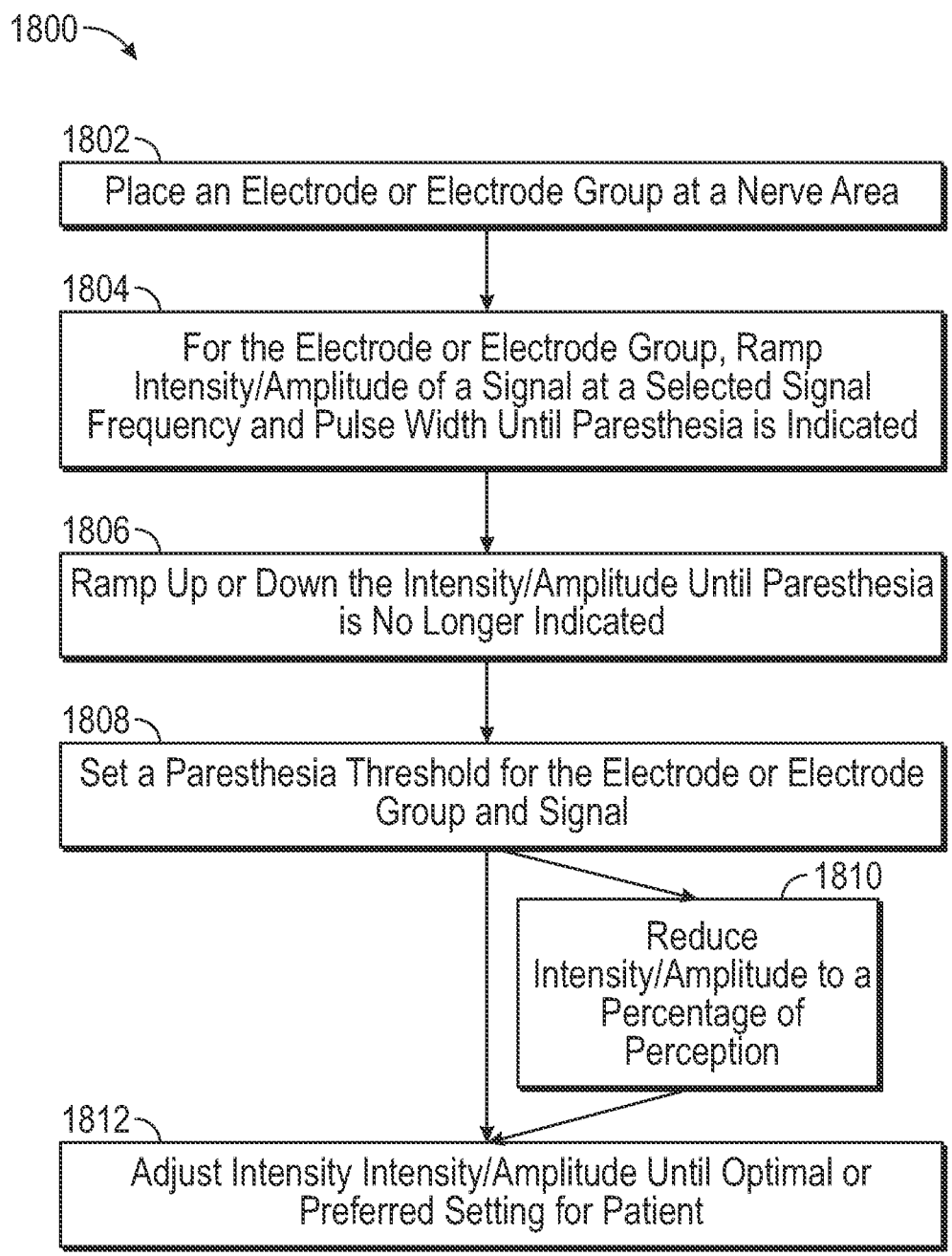

FIGS. 17A, 17B, 17C, 17D, and 17E illustrate conceptually graphs of experimental results indicating how the polarity of the stimulating electromagnetic field signal influenced gene expression; and FIG. 18 illustrates an exemplary patient fitting/setup workflow.

DETAILED DESCRIPTION

This application claims priority to, and benefit of, U.S. Provisional Application No. 62/377,139, filed Aug. 19, 2016, entitled "Method and Apparatus for Multimodal Electrical Modulation Of Pain Using Composite Electromagnetic Fields." Further, this application is a continuation-in-part of co-pending U.S. patent application Ser. No. 15/075,550, filed Mar. 21, 2016, and entitled "Method and Apparatus for Multimodal Electrical Modulation Of Pain." This application is also a continuation-in-part of co-pending U.S. patent application Ser. No. 15/075,565, filed Mar. 21, 2016, and entitled "Method and Apparatus for Multimodal Electrical Modulation Of Pain." Finally, this application is also a continuation-in-part of co-pending U.S. patent application Ser. No. 15/075,582, filed Mar. 21, 2016, and entitled "Method and Apparatus for Multimodal Electrical Modulation Of Pain." The contents of all of these applications are incorporated herein by reference in their entirety for all purposes.

The present disclosure will be more completely understood through the following description, which should be read in conjunction with the drawings. In this description, like numbers refer to similar elements within various embodiments of the present disclosure. The skilled artisan will readily appreciate that the methods, apparatus and systems described herein are merely exemplary and that variations can be made without departing from the spirit and scope of the disclosure.

The oscillatory electromagnetic fields applied to neural structures induce changes in synaptic plasticity upon modulation of two different cell populations: Neurons and glial cells. This is concurrent with the well-known effects on neurons such as action potential generation or blockade by the stimulation of mechanosensitive fibers to mask (or close the gate to) nociceptive signals travelling to the brain. As such, paresthesia is a byproduct and not a pre-requisite to attain pain relief during conventional electrical stimulation. In addition, glial cells are immunocompetent cells that constitute the most common cell population in the nervous system and play a fundamental role in the development and maintenance of chronic neuropathic pain. Glial cells are responsible for monitoring the status of the nervous system by using constant chemical communication with neurons and other glial cells. Microglia are the glial cells in charge of monitoring the brain and spinal cord. Following a nerve (or brain) injury, these cells become activated and respond to any stimulus that is considered a threat to Central Nervous System (CNS) homeostasis. This activation involves morphological changes in the microglia accompanied by changes in chemotaxis and phagocytic activity, as well as the release of chemokines and cytokines that induce a response from the immune system. It has been shown that microglia are the CNS immediate responders to injury. Injury also triggers the activation of astrocytes, glial cells that monitor the synaptic clefts and thus are involved in synaptic plasticity via the regulation of neuro and glial transmitter molecules and involvement of immune cells for synaptic pruning. Astrocyte activation and regulation is sustained for longer time and thus it can be hypothesized that astrocytes play an important role in changes affecting synaptic plasticity in chronic pain. There is experimental evidence that supports this hypothesis. It is worth noting that at the Peripheral Nervous System (PNS), oligodendrocytes, Schwann cells and satellite glial cells, similar to astroglia, play similar roles.

Calcium ions and phosphorylating processes mediated by ATP play an important role in glial response to injury. Electrical impulses induce changes in the concentration of calcium ions in the astrocytes, which propagates between astrocytes via calcium waves. This, in turn, signals the release of transmitters such as glutamate, adenosine and ATP, even after sodium channel blockade, which modulates both neuronal excitability and synaptic transmission. The presence of an external oscillatory electrical field then provides a stimulus for glial cells to affect synapses that have been negatively affected by injury. The electrical field provides a priming response that moves the function of the synapse towards a normal state.

It is possible to electrically stimulate glial cells as their response (glial depolarization, release/uptake of ions, release of glial transmitters) depends on the specific parameters such as amplitude, frequency, phase polarity, waveform shape, and width (in the case of rectangular waveforms) of the stimulation. For example, the release of glutamate from astrocytes may be modulated in proportion to the amount of anodic current administered during biphasic pulsed stimulation. Monophasic cathodic stimulation of hippocampal astrocytes promotes the release of glutamate. The introduction of an anodic component decreases the amount of glutamate released. Given that the glial cells and neurons respond differently to electrical fields; it is then possible to differentially modulate the response of these cell populations with distinctly different electrical parameters. This theory sets a mechanistic basis of multimodal stimulation. Subthreshold stimulation with an electromagnetic field set at an optimum frequency, amplitude, waveform, width and phase may modulate the behavior of glial cells and the way they interact with neurons at the synaptic level. Thus, multimodal modulation provides the ability to control the balance of glutamate and glutamine in a calcium dependent manner and the possibility of modulating such balance in the appropriate manner with electromagnetic fields.

Electromagnetic fields modulate the expression of genes and proteins, which are involved in many processes involving synaptic plasticity, neuroprotection, neurogenesis, and inflammation. A genome-wide expression analysis of ipsilateral DC and DRG tissues obtained from an animal model of chronic neuropathic pain, in which SCS was applied continuously for 72 hours, provided findings that informed development of the multimodal methodologies described below. Without wishing to be bound by theory, the gene expression results indicated that the analgesic effect was likely induced at the molecular level in addition to, or independently of, the electric field blocking or masking nerve signaling. For example, SCS was identified to have upregulated genes for calcium binding proteins (Cabp), cytokines (Tnf, 116, 111b, Cxcl16, lfg), cell adhesion (ltgb) and specific immune response proteins (Cd68, Tlr2), all of which have been linked to glial activation. Modulation parameters, particularly the oscillation frequency and amplitude, may play an important role in the mode of action.

Multimodal Modulation Methodology

According to one exemplary aspect of the disclosure, a method for multimodal modulation utilizes a composite electric field with at least one component oscillating at a frequency higher than that typically used in tonic stimulation. The electrical field of this priming component provides a persistent electrochemical potential that facilitates the stimulation of nerves by another component that is oscillating at a lower frequency. Without being bound by theory, the priming component lowers the threshold for depolarization of nerve fibers while simultaneously modulating glial activation. The priming component also lowers the impedance of the stimulated tissue, which allows for better penetration of the electric field into the neural tissue. The frequent pulsing of the priming component also contributes to a lower threshold for depolarization of nerve fibers via membrane integration of the electrical stimulus. Additionally, the priming component contributes to neuronal desynchronization, which is a mechanism that helps with the reestablishment of neuronal circuits that have been unnaturally synchronized to maintain a nociceptive input into the brain.

In the disclosed prime multimodal modulation technique, a mechanism of depolarization is combined with amplitudes lower or slightly higher than the Paresthesia Threshold (PT), so the patient may or may not experience tingling even though tonic stimulation is being applied. In exemplary embodiments, a priming component of the composite signal provides electrical stimulation at frequencies which will activate the molecular mechanisms that allow for resetting of the synaptic plasticity to a state closer to the one previous to central sensitization induced by injury, thus providing a mechanism for long lasting pain relief.

The Priming Frequency (PF) of a priming component may be set to any frequency above the tonic frequency. In one embodiment, the PF may be set to any frequency between 200 Hz to 100 kHz. When a charged-balanced pulsed rectangular electrical component, e.g., biphasic symmetric, biphasic asymmetric, capacitor coupled monophasic, is used, the Pulse Width (PW) of the priming component may be set as low as 10 µs and as large as allowed by the priming frequency. For example, the maximum PW for a biphasic component with equal PW per phase and a 20 µs interphase delay is 395 µs for PF=1,200 Hz or 980 µs for PF=500 Hz. Either a voltage or current controlled composite signal may be used, although a current controlled signal may be more desirable as such signal does not depend on temporal impedance variations in the tissue being stimulated.

In one exemplary embodiment, a first or priming frequency is between 1000 Hz and 1400 Hz (burst), or between 750 Hz and 1050 Hz (average). In another exemplary embodiment, the first or priming frequency is set to 1200 Hz (burst), or 900 Hz (average). In further exemplary embodiments, each pulse may be provided on a separate program for different groups of electrodes, with a configuration set to allow for individual amplitude variability.

In further exemplary embodiments, a second or tonic component is set at a frequency of about 50 Hz, interleaved into the treatment to account for the average priming frequency, though other tonic values and ranges are contemplated herein, e.g., 20 Hz to 200 Hz, 20 Hz to 100 Hz, 30 Hz to 80 Hz, etc.

As will be discussed in more detail, below, exemplary processes for programming may be configured to determine a program algorithm for one program, followed by matching or setting the algorithm for other programs to be the same or adjusted based on the first program. Additionally, in exemplary embodiments, plural, different priming frequencies may be used, with varying selection of amplitude, pulse width and frequency to relieve pain.

The amplitude of a priming component may be set at a value below a Priming Perception Threshold (PPT), although setting it at or above the PPT is not excluded. The PPT may be found by slowly increasing the amplitude while feedback is obtained from the subject. Once the onset of perception is recorded, then the amplitude of the priming component may be changed to a value which is a percentage of the PPT (% PPT). With an exemplary PF of 1500 Hz, the signal may be then set for a given time, e.g., 10-30 minutes, before an electric component set at a tonic frequency lower than the PF, e.g., 10 Hz to 99 kHz, is applied independently to other electrodes in the lead. In one embodiment, with an exemplary PF of 200 Hz, the tonic frequency may be in the range of approximately 10 Hz to 199 Hz, for example. In the prime mode of stimulation, the tonic frequency will be lower than the priming frequency but is not necessarily limited to a particular range of frequencies below the priming frequency.

The Pulse Width (PW) of a charge-balanced, e.g., a biphasic symmetric, biphasic asymmetric, or capacitor coupled monophasic, pulsed signal can be as low as 10 μs and as large as allowed by the set tonic frequency. In exemplary embodiments, the pulse width may be between about 100 and 500 microseconds, between about 100 and 400 microseconds, between about 150 and 200 microseconds, or any different value, range or combinations of pulse widths.

The signal generation and delivery circuitry may also allow for modifying the duty cycles of pulsed width signals and various schemes in which the time of initial priming can be varied, as well as the times in which the priming signal is on or off relative to the time when the tonic signal is delivered. The amplitude of the tonic electrical component, which could be either voltage or current controlled, may be set above, below or at the Tonic Perception Threshold (TPT). PT may be obtained by increasing the amplitude of the tonic component while getting feedback from the patient. The tonic amplitude may then be set to a value corresponding to a percentage of the TPT (% TPT). In the prime multimodal modulation methods described herein both the priming component and the tonic component may be below 100 kHz, in one embodiment. In another embodiment, the tonic signal may be below 500 Hz. In still another embodiment, the tonic signal may be below 100 Hz. In one embodiment, the ratio of priming component frequency to tonic component frequency may be in the range of 2:1 to 40:1, 4:1 to 40:1, 10:1 to 40:1, 20:1 to 40:1, up to 70:1, up to 140:1, etc. depending on the specific values of the frequencies chosen.

In yet another embodiment of multimodal modulation therapy, the priming component may be biphasic in which the polarity of the first phase of the biphasic prime component may be either cathodic or anodic. With this embodiment, the tonic component may have characteristics that are different from those of the priming component. The tonic component may be biphasic with the polarity of the first phase of the biphasic tonic signal being either cathodic or anodic.

In exemplary embodiments of multimodal modulation therapy, an active recharge mode provides a recovery pulse that applies an equal charge in a direction opposite to the input, thus driving the waveform each way.

The techniques disclosed herein may be achieved with minimally invasive procedures which are preferred over those that require extensive surgical intervention and healthcare expenses although in particular circumstances, a surgical implantation may be required. Electrical stimulation leads, similar to those illustrated in FIGS. 3A and 38, can be used, but other designs having a different number of electrodes, size of the electrical contact, spacing between contacts, and geometrical arrangement of electrodes within an array may be utilized to deliver electromagnetic stimulation to a neural structure. In exemplary embodiments, various electrode and lead configurations provide spacing configured to modulate glial cells and neurons.

In an embodiment, a lead comprises a cylindrical arrangement of multiple electrodes, e.g., between 4 and 16. The diameter of the lead may be small enough to allow for percutaneous implantation into the spinal canal using an epidural needle under standard clinical practice. The electrodes are made of biocompatible materials such as iridium-platinum alloys, which are also resistant to corrosion. For example, a 50 cm long lead implemented with eight electrodes may have a diameter of 1.35 mm, with each cylindrical electrode having a length of 3.0 mm, and a spacing between electrodes of 4.0 mm. Conducting wires may run from the electrodes to the distal part of the lead into metal connectors. The wires may be enclosed within a triple-insulated containment made of a biocompatible durable polymer.

Figure 3A:
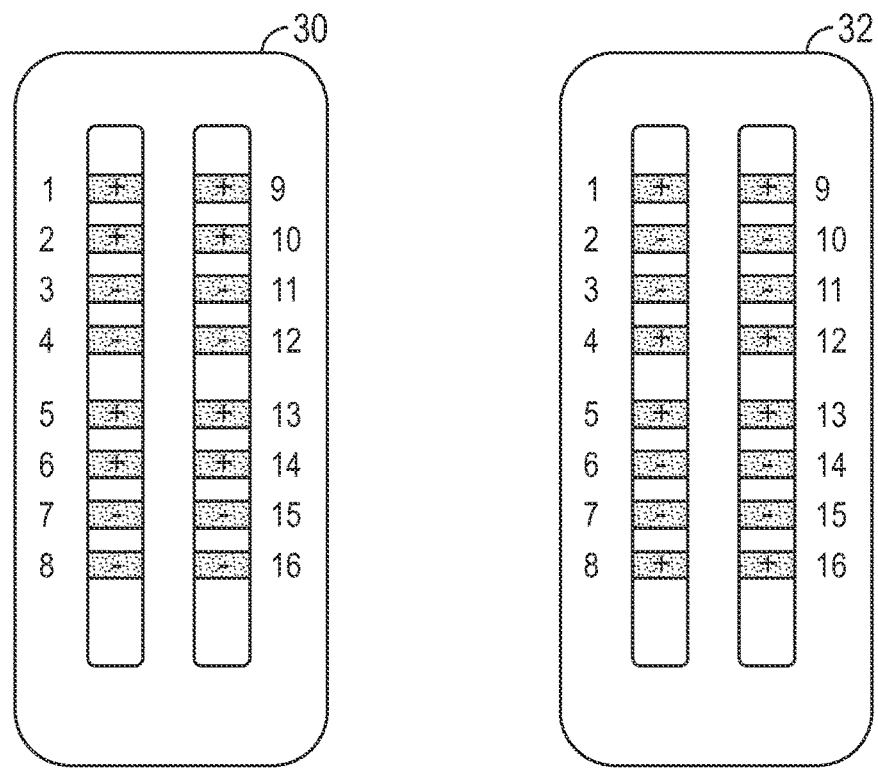
FIGS. 3A and 3B illustrate conceptually electrode arrays that may be utilized with a system in accordance with an embodiment of the present disclosure.

In the case of multimodal modulation of the spinal cord, various multi-contact leads can be positioned in the epidural space to stimulate the cell populations already described. In one particular arrangement, the leads can be positioned parallel to each other, although not necessarily coplanar within the epidural space. FIG. 3A illustrates two eight-contact electrode arrays that can be used for the disclosed multimodal modulation techniques. Note that the polarity of the leads can also be customized during the programming stage, either as bipolar, monopolar, or guarded cathode configurations. Another example of a possible electrode array arrangement is shown in FIG. 38 in which the leads are arranged staggered relative to each other. The customization and optimization of therapy may comprise the positioning of the leads within the epidural space at appropriate vertebral segments in either type of lead arrangement.

Other arrangements may be used to stimulate different places along the spinal canal, e.g., the leads do not need to be parallel. For example, in one arrangement, one lead can be dedicated to deliver a signal at the spinal cord at a given vertebral level, while the other provides a signal either more caudad or cephalad relative to the position of the other lead. Leads can be, in principle, located at any vertebral level in the spinal cord, or could also be positioned peripherally, because the principle behind multimodal modulation applies to peripheral glial cells that survey the axons.

Furthermore, the multimodal stimulation electromagnetic fields location and penetration may be also utilized for customization and optimization of therapy by delivering multimodal stimulation signals to particular arrays of electrodes within each lead by setting monopolar, bipolar, or guarded cathode arrangements of such electrode arrays. For example, therapy for a patient with low back pain that extends into one of the lower extremities may require positioning the stimulation leads in a staggered arrangement within the epidural space along vertebral levels thoracic 8 (TS) and thoracic 12 (T12). An array of electrodes in the more cephalad of the leads may be set to monopolar, bipolar or guarded cathode arrangement. Another array of electrodes in the more caudad of the leads may be set to monopolar, bipolar or guarded cathode arrangement. The clinician will be able to customize the electrode array setting in a methodical manner such that therapy can be optimized for based on feedback from the patient.

Figure 14:
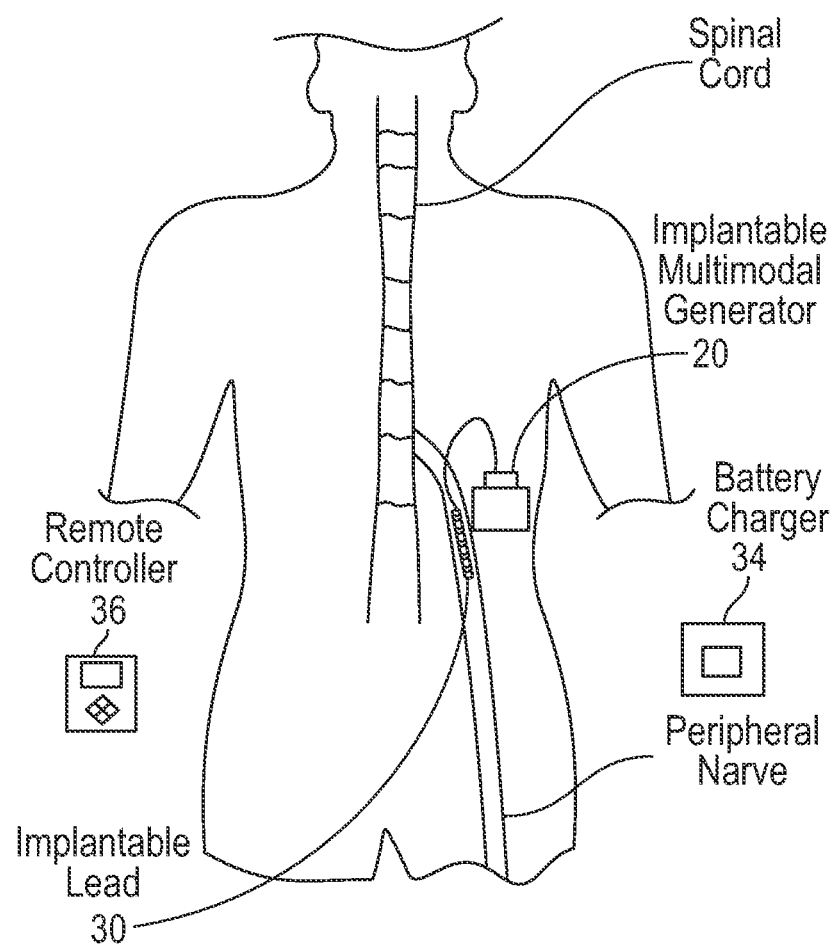
FIG. 14 illustrates conceptually the placement of an implantable system with a human subject in accordance with an embodiment of the present disclosure.

Optionally, pain relief may also be used by position the leads in the neighborhood of a peripheral nerve as illustrated in FIG. 14. Peripheral Nerve Stimulation (PNS) is an alternative therapy for chronic pain in which a target nerve has been identified to be the source of pain. The current understanding of the therapeutic effects of PNS is also based on the gate control theory. However, axons of sensory neurons in peripheral nerves are surrounded by glial cells that are known to respond accordingly to the frequency characteristics of a stimulus.

Multimodal peripheral nerve stimulation involves the positioning of one or more stimulation leads around or in the neighborhood of a target nerve. The leads are connected to a signal generator with multimodal capacity as described herein. Multimodal stimulation is delivered to the neural tissue consisting of neuron axons and their corresponding glial cells (Schwann cells) according to the principles and methods described in this application. The leads may implant to be positioned around the target nerve using an invasive surgical approach or percutaneously utilizing a needle cannula.

Alternatively, as would be the case for the stimulation of target nerves that are close to the skin surface (such as the vagus nerve, nerves in the joints of the extremities, etc.) the leads may be arranged inside a conductive biocompatible pad for delivery of the multimodal electromagnetic field transcutaneously. This embodiment constitutes Transcutaneous Electrical Nerve Multimodal Stimulation (TENMS). In this embodiment, the priming high frequency component of the multimodal signal lowers the impedance of the skin and subcutaneous tissue and allows for better penetration of the tonic signal. The priming signal also provides a modulating signal for perisynaptic glial cells in the neuromuscular junction. These cells are known to discriminate different stimulation patterns and respond accordingly, thus allowing for modulation of the synapse with multimodal stimulation. The tonic component of the multimodal signal is used to stimulate the neuronal axon at lower thresholds.

Systems Components

Figure 1:
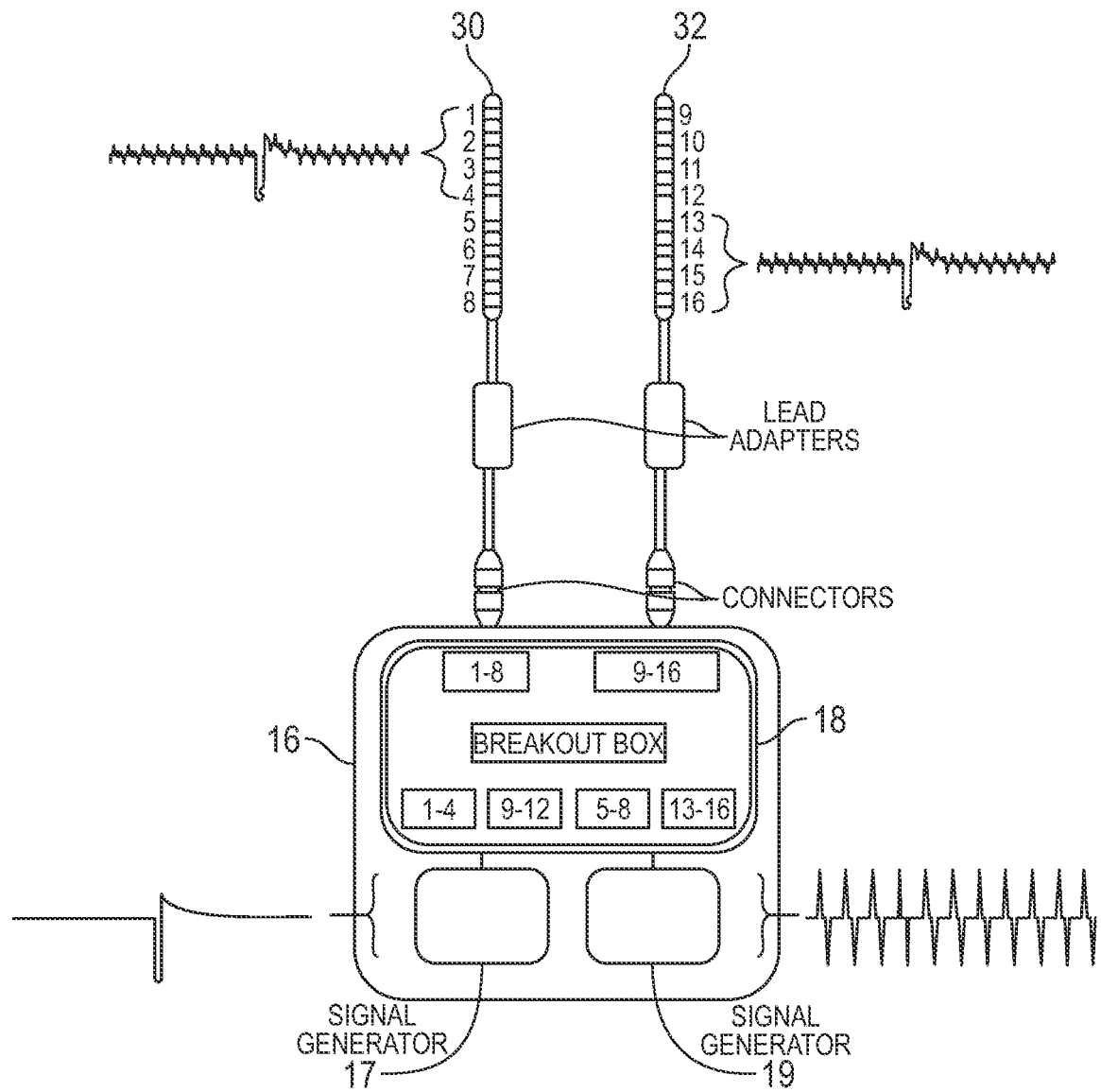
FIG. 1 is a schematic diagram illustrating an apparatus for pain management in accordance with an embodiment of the present disclosure.

FIG. 1 illustrates conceptually an embodiment of a multimodal stimulation system that may be utilized to perform the methods disclosed herein. The system comprises a pair of electrical leads 30 and 32, each of which may be implemented with an array of electrode contacts, a breakout box 18 and signal generators 17 and 19, as illustrated. Breakout box 18 is electrically coupled to leads 30 and 32 and signal generators 17 and 19 through appropriate connectors. The breakout box 18 and signal generators 17 and 19 may be placed in an enclosure referred to as an External Stimulator Unit (ESU) system 16. Each of generators 17 and 19 delivers a particular signal with parameters that can be set separately for each other. Each of generators 17 and 19 may have the functional characteristics and architecture elements similar to generator 20 described herein without an exterior enclosure suitable for implantation into a patient. In one embodiment, system 16 may also include one or more of the modules described herein with reference to Implantable Multimodal Generator 20 and FIG. 2.

The ESU system 16 is electrically coupled to electrical leads, each of which may be implemented with an array of electrode contacts. In an embodiment, a pair of leads 30 and 32 is coupled to the ESU 16 using appropriate connectors as illustrated in FIG. 1. In another embodiment, a single lead implemented with an array of electrodes can be used. In a configuration for performing prime multimodal modulation, one of generators 17 or 19 may be configured to deliver a priming component, for example 1,200 Hz, and the other generator may be configured to deliver a tonic component, e.g., at 50 Hz. The breakout box 18 may be used to reconfigure the delivery of signals to the proper electrode contacts in leads 30 and 32. In the embodiment illustrated in FIG. 1, the electrode contacts 1-8 in electrode array 30 can be split such that electrode contacts 1-4 deliver a first signal, e.g., a tonic signal, different than a second signal delivered at electrode contacts 5-8 thereof, e.g. a priming signal. Similarly, electrode contacts 9-16 of electrode array 32 may be split such that electrode contacts 9-12 thereof deliver a signal similar to that delivered by electrode contacts 1-4 in electrode array 30, while electrode contacts 13-16 thereof deliver a signal similar to that delivered at electrode contacts 5-8 in electrode array 30, as illustrated.

Implantable Multimodal Generator

Figure 2:
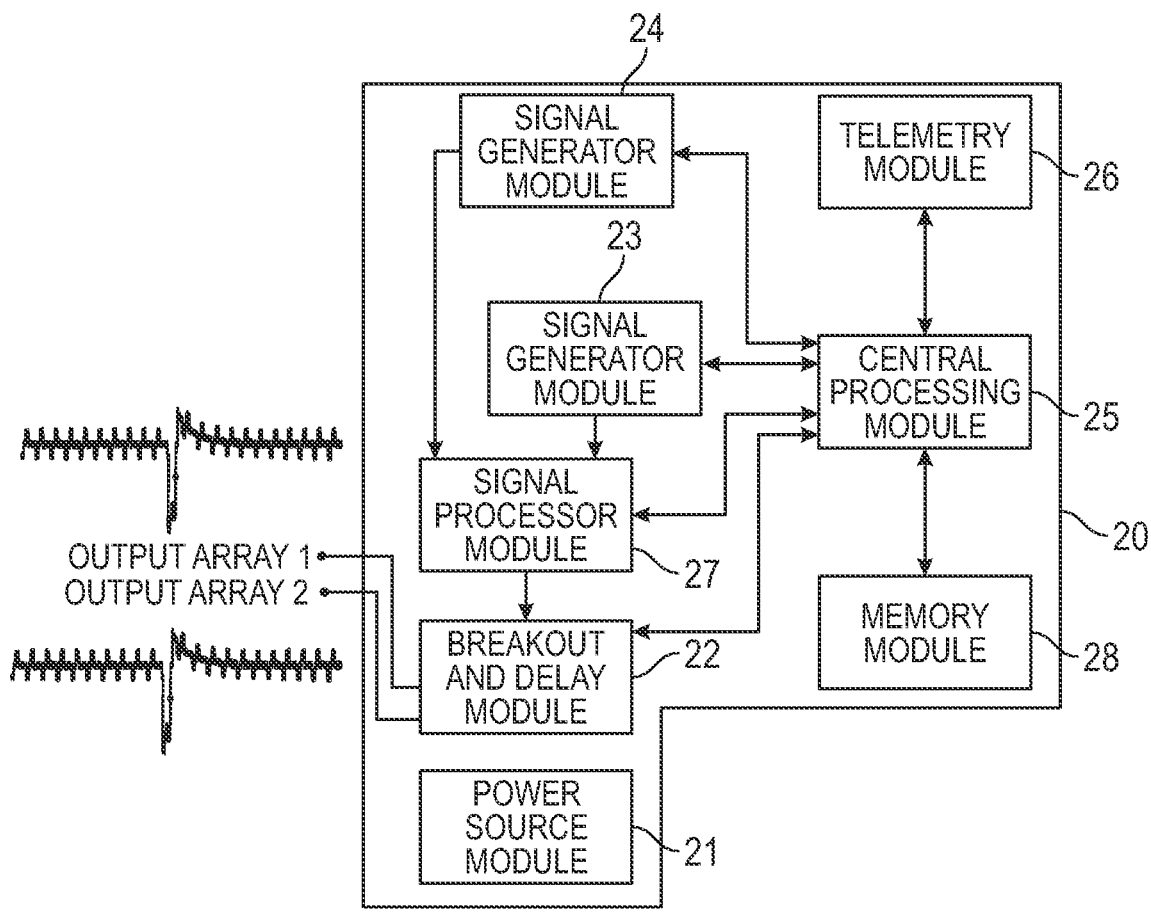
FIG. 2 illustrates a schematic circuit diagram of an implantable multimodal modulation device that may be utilized with a system in accordance with an embodiment of the present disclosure.

FIG. 2 illustrates conceptually a block diagram of the elements comprising an Implantable Multimodal Generator (IMG) 20. The generator circuitry may be hermetically sealed in a housing made of a durable biocompatible material, such as stainless steel or titanium. The generator 20 has an output interface for establishing electrical connection with arrays of electrodes implemented within the previously described leads 30 and 32 that deliver the multimodal signals to glial cells and neurons. In one embodiment, the implantable multimodal generator 20 comprises a central processing module 25, a memory module 28, a telemetry module 26, a power source module 21, signal generator module 23, signal generator module 24, and a Breakout and Delay module 22, and signal processor 27, including the output interfaces thereof. In embodiments, the elements of implantable multimodal generator 20 may be interconnected as illustrated in FIG. 2, or, may be connected through a central bus, which enables intercommunication amongst all components depending upon the actual implementation.

The central processing module 25 may be implemented with a microprocessor integrated circuit or may comprise reduced functionality small-scale logic, but in either implementation includes a wireless transceiver functionality that enables bidirectional wireless communication of information with an external programmer unit (not shown) or a user-controlled remote 36.

The memory module 28, which may be implemented with either RAM or ROM memory, may be used to store a modulation program, executable by central processing module 25, which generates functional information of the generator 20. The central processing module 25 is able to store and retrieve information from a memory module 28 as commanded by the user.

The telemetry module 26 is used to communicate via a wireless protocol with the external programmer unit (or control remote) and includes transceiver circuitry in order to conduct wireless communications with devices remote from generator 20 according to any number of established wireless protocols.

The power source module 21 may comprise a rechargeable or a non-rechargeable battery and electronic circuitry that distributes power from the battery to all the other components in the implantable multimodal generator 20.

The signal generator module 23 comprises electronic circuitry that allows the delivery of charge-balanced waveforms of any waveshape, including but not limited to biphasic or monophasic pulses, sinusoidal trains, sawtooth trains, triangle trains, and bursts thereof.

In one embodiment, signal generator module 23 comprises electronic circuitry that allows the delivery of noise signals, such as white noise, with a constant power spectral density, or pink noise, with equal energy in octave intervals, or other noise signals in which the energy within the signal spectrum is distributed in other patterns. In one embodiment, a noise signal may be used as the priming component in the techniques disclosed herein. The signal generator module 23 is able to deliver these waveforms at frequencies ranging from 1 Hz to 100 kHz. For pulse delivery, the signal generator module 23 is able to deliver rectangular pulse waves over a range of widths, e.g., as small as 1 µs and as large as 250 ms, depending on frequency. The signal generator module 23 is further capable of generating a range of interphase delays. The signal generator module 23 is designed to deliver a signal, with amplitude, which is either voltage controlled or current controlled, over a range of values, e.g., 0 V to 30 V or 0 mA to 30 mA, respectively. The signal generator module 23 is also able to generate pulses with a duty cycle. The signal generator module 23 is controlled by the central processing module 25 according to parameters selected by the user in an external programmer unit (or control remote). The signal generator module 23 may be implemented with analog or digital circuitry or a combination thereof.

Signal generator module 24 may be structurally and functionally similar or dissimilar to signal generator module 23, and may be independently controlled and programmed.

Signal processor 27 may be implemented with a special-purpose digital signal processor (DSP), or, may comprise a programmable general-purpose DSP. Signal processor 27 may be implemented with any number of commercially available signal processing integrated circuit components having a specialized instruction sets and processor capable of performing algorithmic manipulation of one or more signals input thereto.

Signal processor 27 receives signals from signal generator modules 23 and 24 and is programmable to execute a multitude of algorithms for combining the separate signals into a single composite signal, including any of amplitude modulation, frequency modulation, signal summing, signal syncing, phase modulation, convolution, etc., or any combination thereof, as well as generation of customized signals from wave tables or digital oscillators in real time in response to user input data. Signal processor 27 may have associated therewith a scratchpad memory area used for local storage of data and program variables when performing signal processing or other tasks. In addition, signal processor 27 may also comprise specialized analog circuitry such as filters, control circuitry, and circuitry for creating a composite signal from signals from signal generator modules 23 and 24. Depending on whether the output of the signals generated by signal generator modules 23 and 24 is analog or digital, signal processor 27 may also include its own analog-to-digital converter and digital-to-analog converter for converting any input signals into the proper format for processing and converting the signal into the proper format for output to breakout and delay module 22.

The breakout and delay module 22 comprises an accurate timer electronic circuitry that can slave one of signal generator modules 23 or 24 to the other, so that a delay can be produced between signals generated therefrom such that a synchronized delivery of such signals can be programmed by a user. The breakout and delay module 22 also incorporates electronic circuitry, called breakout, that allows for the user to select an option in which the output array 1 delivers a signal to all top (rostral during spinal cord stimulation) electrode contacts of a pair of electrode arrays (for example, tonic 50 Hz, 250 µs pulse width, 3.0 mA), while output array 2 delivers a signal to all bottom electrode contacts of a pair of electrode arrays (for example, a priming signal of 1,200 Hz, 100 µs pulse width, 3.5 mA). An example of this option is shown in FIG. 3A.

Figure 3B:
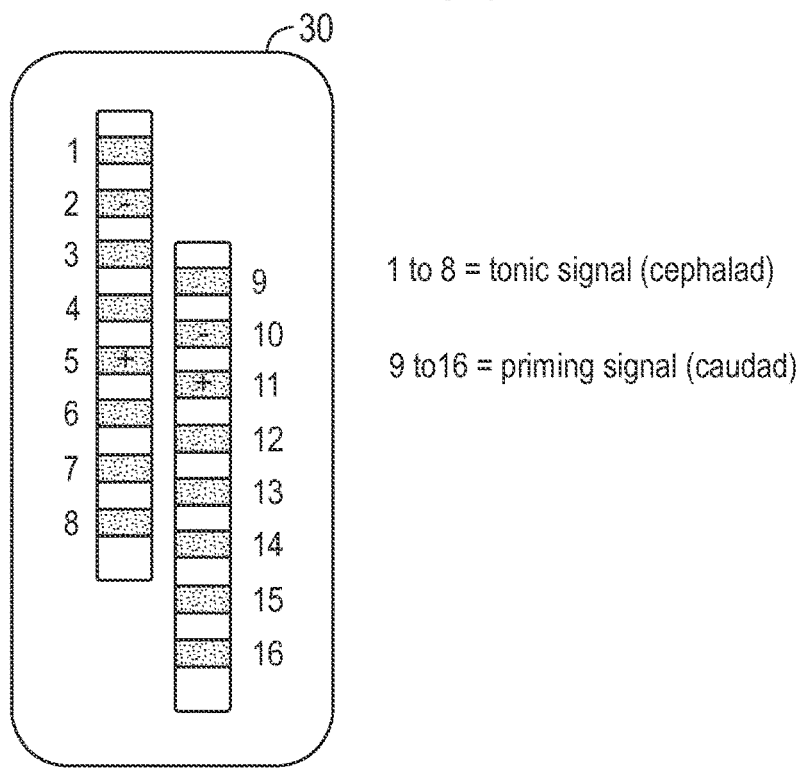

Another option is one illustrated in FIG. 3B where the breakout option can be bypassed. In that case, all contacts in a given electrode array will be set at the same modulation parameters as delivered by, for example, signal generator module 23. All contacts in the other electrode array will be set to the same modulation parameters as delivered by the other signal generator module. In embodiments in which the same composite signal is provided as outputs to both array 1 and array 2, the functionality of breakout and delay module 22 may be performed entirely by signal processor 27, obviating the need for breakout and delay module 22, assuming the appropriate output interface is used to properly couple the outputs of signal processor 27 to the electrode arrays.

In one embodiment, all or most of the functional blocks of generator 20 may be fabricated on a single integrated circuit chip including a microprocessor and associated memory, wireless transducer and one or more digital oscillators. Alternatively, the digital oscillators may be replaced with wave tables having stored therein mathematical descriptions of various waveform data values, which are convertible into analog signals using a digital to analog converter, integrated into or associated with the processor module 25 or signal generator modules 23 or 24, depending on their respective implementations. Such wavetables may be stored in processor module 25 or memory module 28.

In other embodiments, the various modules of IMG 20 may communicate over a central bus internal thereto or may have dedicated direct connections there between, or any combination thereof.

In one embodiment, IMG 20 or ESU 16 may be programmed by a clinician using software that allows control of all the aspects of the system. The software may be accessible in a computer-based interface called the Clinician Programmer (CP) software. The software may be implemented with wireless communication protocols for remote access of the IMG 20 or ESU 16. ESU 16 may also be provided with a network port such as a USB or micro-UBS port for interacting with the CP. In the case of IMG 20, the CP software enables the clinician to communicate with central processing module 25 to define a set of parameters, e.g., any of amplitude, frequency, phase, phase polarity, waveform shape, and width (rectangular waveform), etc., of the signal generated by signal generator modules 23 or 24 and to further define the parameters of their relative timing by defining the operational parameters of breakout and delay module 22. Such defined parameter sets may be stored as one or more configuration programs in memory module 28 or in memory associated with central processing module 25.

In one embodiment, one or more configuration programs may be stored in memory associated with remote controller 36 and the parameters thereof transmittable to IMG 20 via telemetry module 26 for control of generator modules 23 or 24 and of breakout and delay module 22. The CP software may enable the clinician to further define which parameter the patient my control with the remote controller 36 and to define any limits on such parameter.

For example, the clinician can set and store a configuration program #1 with parameters that provides prime multimodal stimulation consisting of priming with a biphasic symmetric rectangular pulsed signal component set at 1,200 Hz, 150 μs PW, and current-based amplitude set as a % PPT, and a tonic signal component delivering biphasic asymmetric pulses (rectangular and exponentially decaying phases) at 50 Hz, 400 μs PW, and current-based amplitude set as a % PT. The composite signal can be delivered to a particular set of electrodes in the leads.

The clinician can also set and store a configuration program #2 that provides prime multimodal stimulation consisting of a priming with biphasic symmetric rectangular pulses at 900 Hz and 300 μs PW and tonic signal component delivering biphasic symmetric rectangular pulsed at 100 Hz and 400 μs PW and each set at its own current-based amplitude set a particular % PT. These signals can be delivered to a particular set of electrodes in the leads which may be different to that used in configuration program #1. The system allows for setting and storing additional configuration programs deemed necessary for the clinician and according to the storage capacity of the memory module 28.

Limited control of the multimodal configuration programs may be available to the patient via a remote controller 36. In one embodiment, the clinician can access one or more configuration programs using the CP to control any of the parameters of a configuration program already stored in the ESU 16 or IMG 20. The patient may be able to browse and/or select any available configuration program with the remote controller The patient may be able to change the current-based amplitude of any particular configuration program up to a particular setting determined by the PPT or PT in order to optimize pain relief, for example. Note that the remote controller 36 may be provided with a simple interface, such as a selector switch, or dial to select the appropriate configuration program, or a more sophisticated user interface including a visual display with directional keys or touch sensitive menus.

In the embodiments described herein, the option exists for user feedback and control of the system through the programming device. As stated above, the initial settings for priming and tonic frequencies will be programmed by the physician or a clinical field engineer. After this point, the device can allow the patient to change many settings, including the priming and tonic frequencies, parameters of either frequency such as amplitude, duty cycle, pulse width, or phase. In an embodiment, the patient will be able to adjust the tonic stimulation frequency from its initial setting to any frequency between 10 Hz and the priming frequency (fp) minus one. Using the above example of a priming frequency of 1,200 Hz, the tonic frequency could be adjusted between 10 Hz and 1,199 Hz.

In another embodiment, the patient will be able to alter the amplitude of the tonic amplitude, with the range of amplitudes limited between zero and the amplitude of the Priming Stimulation. The patient may also be able to alter the pulse width and duty cycle of either the priming stimulation or the tonic stimulation when the stimulation waveform is comprised of discrete pulses separated by latent periods. These values will be limited by the selected frequencies. The frequency of stimulation determines the time between pulses (herein defined as the period). Due to the requirement of charge balancing, the pulse width can be no larger than the period divided by two. Thus, the patient can shift the pulse width between a minimum value of 10 μs and half the period.

The final patient-controlled aspect is the phase of the waveforms. In this embodiment, the patient will be able to shift the tonic stimulation or priming stimulation throughout its period. A phase of zero would correspond to a pulse occurring at the start of a duty cycle and the remainder of the cycle being void of stimulation. The user can shift the location of that pulse to any point along the duty cycle, with the phase being confined to a maximum value equal to the period. The phase shift of a pulse through its period creates different constructive effects of the electric fields or the signals themselves. This will result in a waveform that appears unique to the neural tissue, despite being comprised of the same priming and tonic frequencies. The purpose of allowing patients to adjust these parameters is to provide each patient with increased control over their pain relief.

Figure 4:
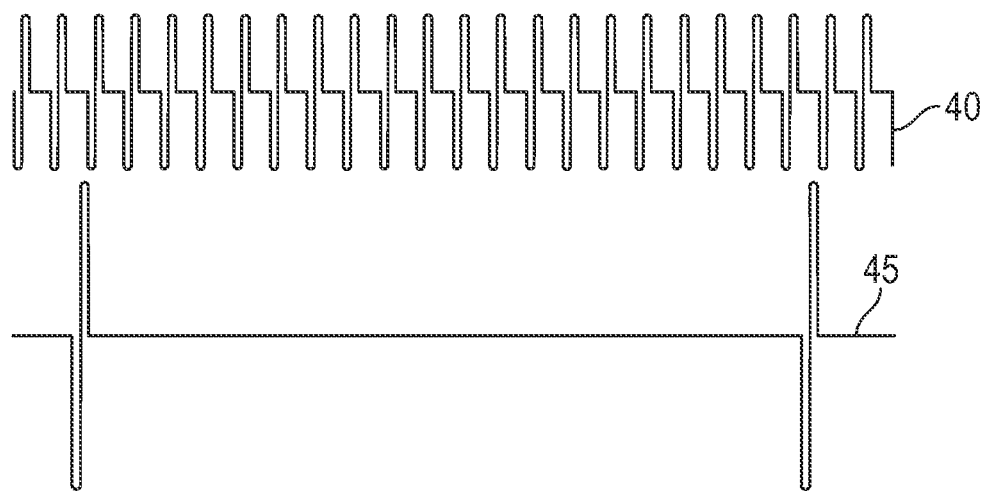
FIG. 4 illustrates conceptually a pair of traces representing signals that may be used in an example of prime multimodal modulation in accordance with an embodiment of the present disclosure.

FIG. 4 illustrates conceptually a pair of traces representing signals 40 and 45 used in an example of prime multimodal modulation. Signal 40 functions as a priming electrical component and may comprise, for example, biphasic rectangular pulses with a frequency of 1,200 Hz, PW=200 μs and interphase delay of 20 μs (though other delays are considered herein, e.g., an 80 microsecond delay between the therapy pulse and the recharge/recovery pulse, with a 40 microsecond gap between the end of the recovery pulse and the next stimulation pulse (e.g., for exponentially decaying recovery pulse)). Signal 45 functions as the tonic component and may comprise, for example, biphasic rectangular pulses with a frequency of 50 Hz, PW=200 μs and interphase delay of 20 μs. In this example, the amplitude of the tonic component is set to be larger than the amplitude of the priming component. Signals 40 and 45 have been offset in FIG. 4 for visual clarity. Signals 40 and 45 may be used to generate a composite signal using the system and techniques described herein.

Figure 5:
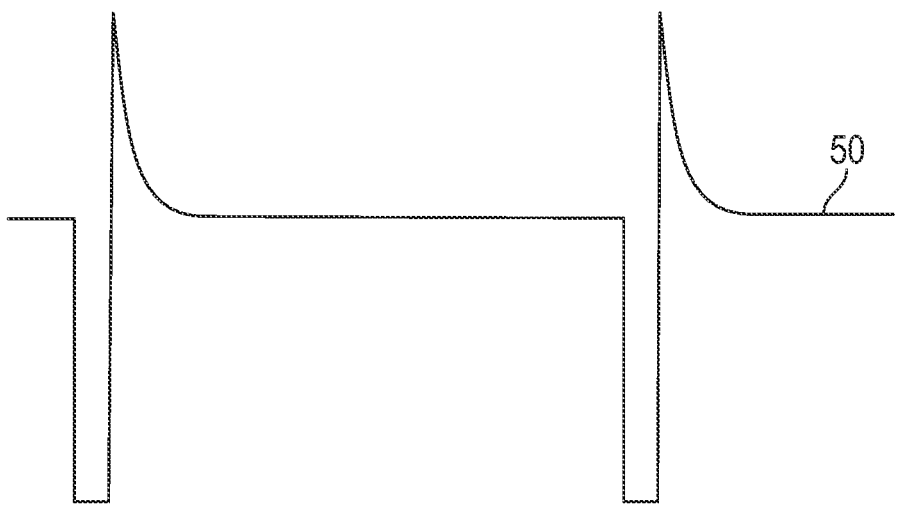
FIG. 5 illustrates conceptually a pair of traces representing signals that may be used in an example of prime multimodal modulation in accordance with an embodiment of the present disclosure.
Figure 5:
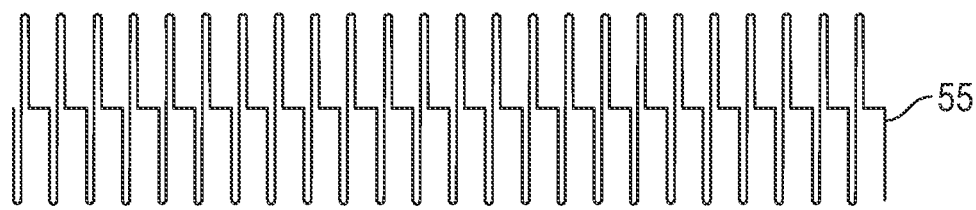

FIG. 5 illustrates conceptually a pair of traces representing signals 50 and 55 used in an example of prime multimodal modulation. Signal 55 functions as a priming electrical component and may comprise, for example, biphasic rectangular pulses with a frequency of 1,200 Hz, PW=150 μs and interphase delay of 20 μs. Signal 50 functions as the tonic component and may comprise, for example, biphasic asymmetric rectangular/exponential decay pulses with a frequency of 50 Hz, PW=400 μs and interphase delay of 20 μs. In this example, the amplitude of the tonic component is set to be larger than the amplitude of the priming component. Signals 50 and 55 may be used to generate a composite signal using the system and techniques described herein.

Figure 6:
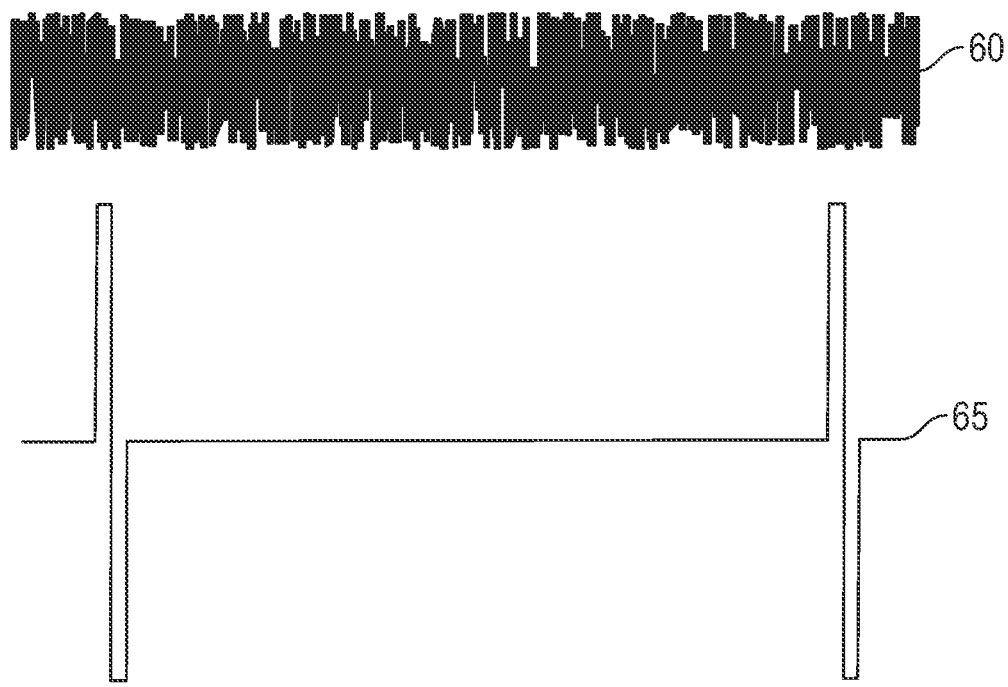
FIG. 6 illustrates conceptually a pair of traces representing signals that may be used in an example of prime multimodal modulation in accordance with an embodiment of the present disclosure.

FIG. 6 illustrates conceptually a pair of traces representing signals 60 and 65 used in an example of prime multimodal modulation. Signal 60 functions as a priming electrical component and may comprise, for example, white noise of a particular maximum amplitude. Signal 65 functions as the tonic component and may comprise, for example, biphasic symmetric rectangular pulses with a frequency of 50 Hz, PW=400 μs and interphase delay of 20 μs. In this example, the amplitude of the tonic component is set to be larger than the amplitude of the priming component. Note that in FIGS. 4-6 the signals representing the tonic and priming waveforms are offset for visual clarity, such offset not meant to be limiting in any matter. Signals 60 and 65 may be used to generate a composite signal using the system and techniques described herein.

The ESU 16 or IMG 20 may deliver multimodal stimulation using a single composite modulation/stimulation signal, which has rhythmically varying characteristics, and, therefore, alternating magnetic field characteristics which achieve the same results as when combining two separate signal components. In such an embodiment, a composite signal characterized by typically alternating characteristics is utilized to obtain the same stimulation and modulation of the interaction between glial cells and neurons. Such a composite signal may be generated by signal processor 27 which is capable of executing a multitude of algorithms for combining separate signals into a single composite signal including any of amplitude modulation, frequency modulation, signal summing, signal syncing, phase modulation, or convolution or any combination thereof, as well as and generation of customized signals from wave tables or in real time, such composite signals having any of periodic or aperiodic characteristics. In addition, pulse width modulation may be used to create a composite signal having variably changing harmonic energy content may similarly be utilized to achieve the desired multimodal stimulation of glial and neuronal cells.

Figure 7:
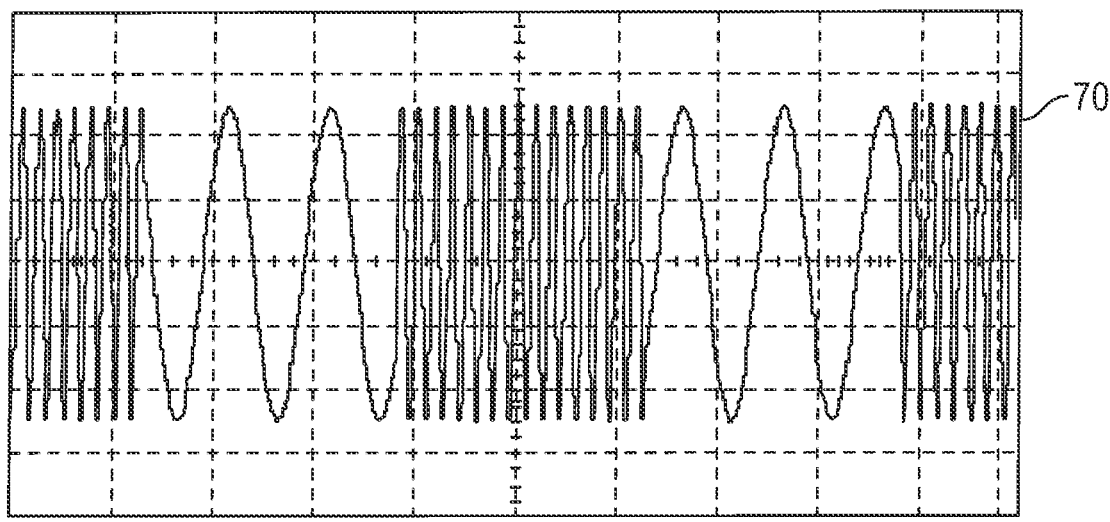
FIG. 7 illustrates conceptually a frequency modulated signal, with a carrier frequency larger that the modulating frequency, that may be utilized for multimodal modulation in accordance with an embodiment of the present disclosure.

FIGS. 7-12 illustrate conceptually example of multimodal composite signals formed by frequency modulated, dual combined sinusoidal, dual combined biphasic rectangular pulses, frequency changing signals, and white noise combined with low frequency pulses, respectively, that may be utilized for multimodal modulation. FIG. 7 illustrates conceptually a frequency modulated composite signal 70 in which the priming signal component thereof is delivered for a given period of time before the tonic signal component thereof is delivered for a given period of time not necessarily equal to the period of time in which the priming component was delivered. I an illustrated embodiment, composite signal 70 may be formed from a sinusoidal priming component at 1,200 Hz delivered for 1 ms followed by a sinusoidal tonic component at 180 Hz delivered for 2 ms. Utilizing the user interface described herein, the user may be able to control the frequency, amplitude and duration of each priming signal and tonic signal component as described herein.

Figure 8:
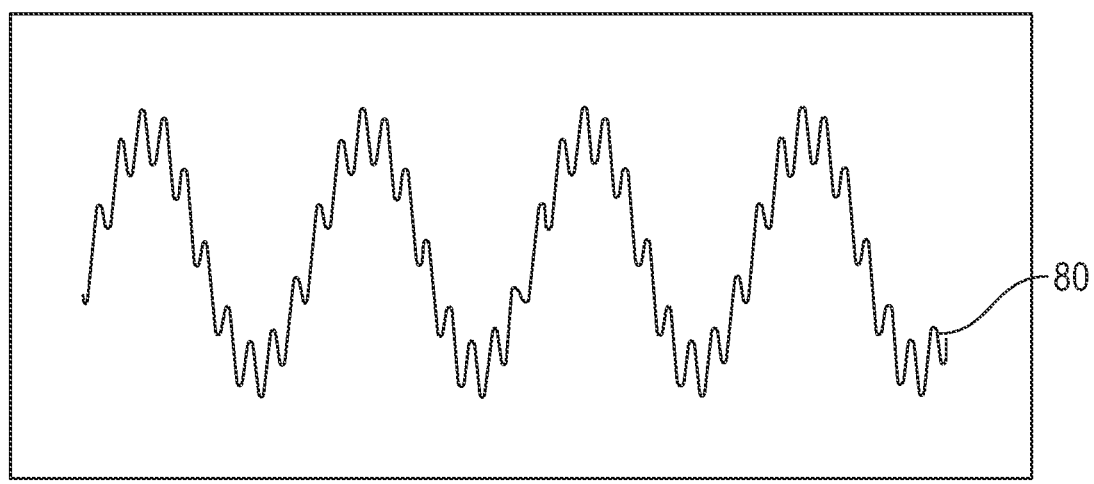
FIG. 8 illustrates conceptually a frequency modulated signal, with a carrier frequency smaller than the modulating frequency, that may be utilized for multimodal modulation in accordance with an embodiment of the present disclosure.

FIG. 8 illustrates conceptually a double sinusoidal composite signal 80 in which the priming component is of lower amplitude and convoluted into the tonic component. In an illustrated embodiment, composite signal 80 may be formed from a sinusoidal tonic component at 100 Hz, and a sinusoidal priming component at 1,200 Hz, with the tonic component having an amplitude that is eight times the amplitude of the priming component. Utilizing the user interface described herein, the user may be able to control the frequency, amplitude and phase shift of each component as described herein.

Figure 9:
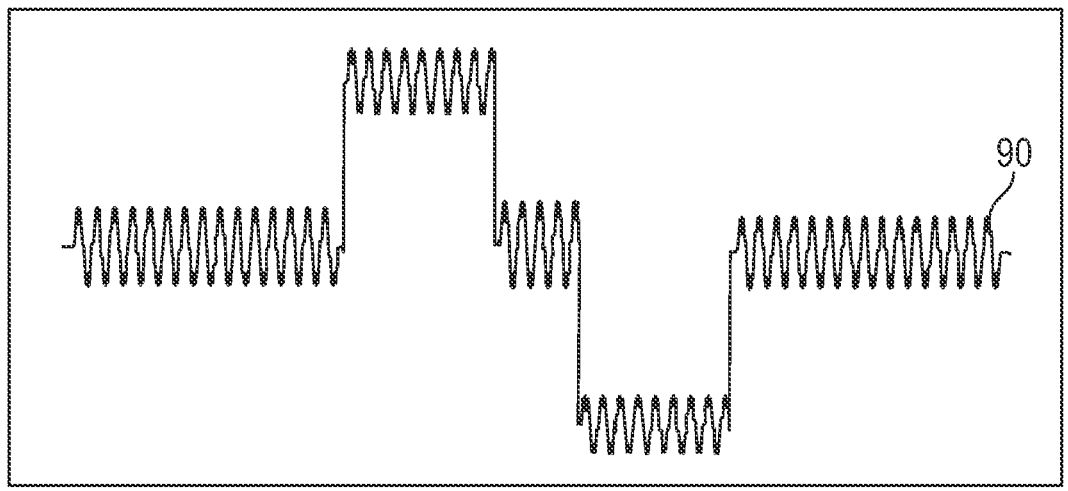
FIG. 9 illustrates conceptually a composite signal, biphasic pulse example, that may be utilized for multimodal modulation in accordance with an embodiment of the present disclosure.

FIG. 9 illustrates conceptually a composite signal 90 made of two biphasic rectangular signals. The priming component is of lower amplitude than the tonic component, and is convoluted with the tonic signal. In an illustrated embodiment, composite signal 90 may be formed from a priming signal at 10,000 Hz and 50 μs PW convoluted in a 250 Hz biphasic rectangular signal with a 900 μs PW, with the tonic component having an amplitude that is ten times the amplitude of the priming component. Utilizing the user interface described herein, the user may be user will be able to control the frequency, amplitude and phase shift of each component as described herein.

Figure 10:
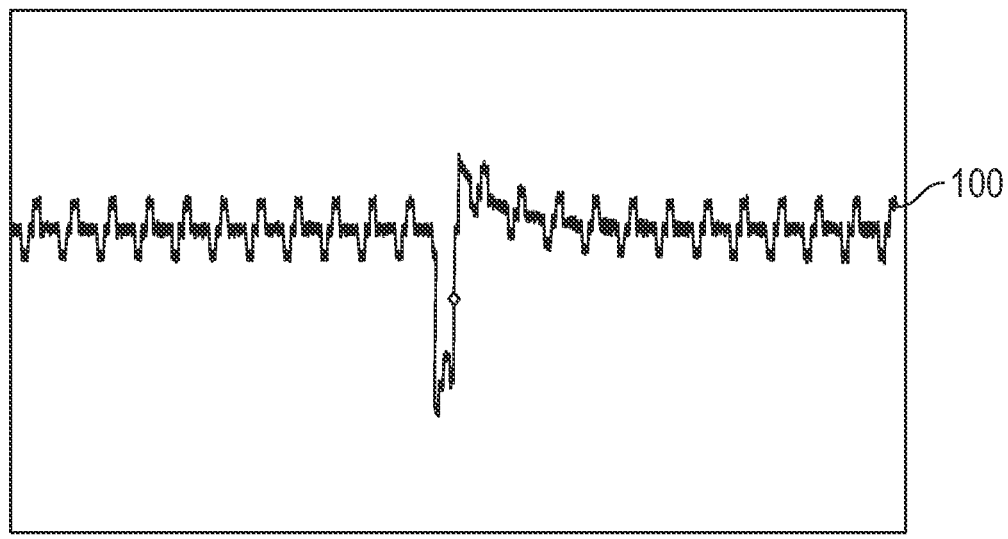
FIG. 10 illustrates conceptually a composite signal with a rectangular biphasic priming component and an asymmetric biphasic tonic component that may be utilized for multimodal modulation in accordance with an embodiment of the present disclosure.

FIG. 10 illustrates conceptually a composite signal 100 made of two biphasic rectangular signals. The priming component is of lower amplitude than the tonic component, and is convoluted with the tonic signal. In an illustrated embodiment, composite signal 100 may be formed from a priming signal at 1,200 Hz and 150 μs PW convoluted in a 50 Hz biphasic asymmetric rectangular/exponential decay signal with a 400 μs PW, with the tonic component having an amplitude that is five times the amplitude of the priming component. Utilizing the user interface described herein, the user may be able to control the frequency, amplitude and phase shift of each component as described herein.

Figure 11:
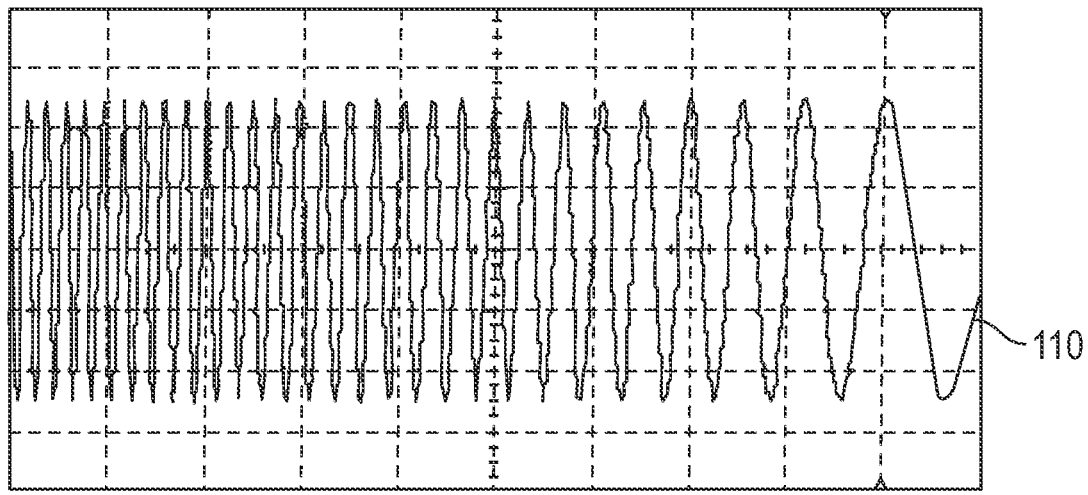
FIG. 11 illustrates conceptually a composite signal with a continually changing frequency that may be utilized for multimodal modulation in accordance with an embodiment of the present disclosure.

FIG. 11 illustrates conceptually a frequency changing composite signal 110 in which the priming component is delivered initially at a frequency larger than the tonic component and then decreases for a given time to the tonic component frequency before a new signal cycle is started. An example may comprise a starting priming frequency of 1,000 Hz, which is rolled down to a tonic frequency of 200 Hz within a 50 ms period, while the amplitude is kept constant. In an illustrated embodiment, composite signal 110 may be formed from a linear or non-linear change in amplitude, as the signal is rolled down from the priming frequency into the tonic frequency. Utilizing the user interface described herein, the user may be able to control the frequency, amplitude and of each component and the roll down time as described herein.

Figure 12:
FIG. 12 illustrates conceptually a composite signal with a white noise priming component summed to a symmetric biphasic tonic component that may be utilized for multimodal modulation in accordance with an embodiment of the present disclosure.

FIG. 12 illustrates conceptually a composite signal 120 in which the priming component is noise and is convoluted with a biphasic symmetric rectangular tonic component. In an illustrated embodiment, composite signal 110 may be formed from a noise amplitude equivalent to one third of the tonic component amplitude with a tonic frequency of 100 Hz and 200 μs PW. The tonic component may be delivered randomly and non-linearly within a 10-500 Hz range in order to create a stochastic resonance effect. In embodiments utilizing stochastic resonance for the tonic component, a pseudorandom signal generation technique may be required. For example, randomization can be obtained with a series of Zener diodes and transistors to create a pseudorandom signal which is based on the random movement of electrons through the circuit.

In some embodiments, randomization can be obtained out of the harmonic oscillations of a quartz oscillator and a timing circuit set to various pseudorandom counting parameters. In other embodiments, a Peltier-based thermocouple can be used to generate randomization based on the thermal noise of the body of the patient. Those skilled in the art will appreciate that many other digital or analog circuit based configurations may be utilized for achieving random numbers. Once obtained, random numbers may be used to generate a digital high or low signal, creating a random series of tonic pulses for application to the neural tissue. Such randomization circuits can also be used to generate noise that approximates true white noise, pink noise, blue noise, brown noise, gray noise, or any other distributions of energy within the frequency spectrum.

Utilizing the user interface described herein, the user will be able to control the frequency, amplitude and phase shift of each component as described herein.

In accordance with an embodiment of the present disclosure, the central processor module 25 of multimodal generator 20 may access stored numeric data mathematically describing wave shapes for one or more signals and may generate from such data step functions emulating signals at different frequencies. The processor performs algorithmic manipulation of such data to achieve the desired signal processing results. Digital to analog converters associated with the central processing module 25 may convert the processed signal into a single output having the correct amplitude for coupling to one or both electrodes 30 and 32. In this manner, the interactive effects of two separate signals may be achieved with a single electrical composite signal capable of stimulating/modulating the interaction between glial cells and neurons in a manner which emulates the use of two separate signals.

In composite signals emulating a frequency modulated prime multimodal modulation signal, either constituent signal component, e.g., the priming signal or the tonic signal, may function as the program or carrier signals in a frequency modulation algorithm. For example, a frequency modulated multimodal signal can have a carrier frequency larger (e.g., 1,000 Hz) than the modulating frequency (e.g., 50 Hz) resulting in a stimulating signal, as illustrated in FIG. 7. In another example, a frequency modulated multimodal signal can have a carrier frequency smaller (e.g., 50 Hz) than the modulating frequency (e.g., 1,000 Hz) resulting in a stimulating signal as illustrated in FIG. 8. In these embodiments, the tonic component may be delivered randomly and non-linearly within a 10-500 Hz range in order to create a stochastic resonance effect as described herein.

Figure 13:
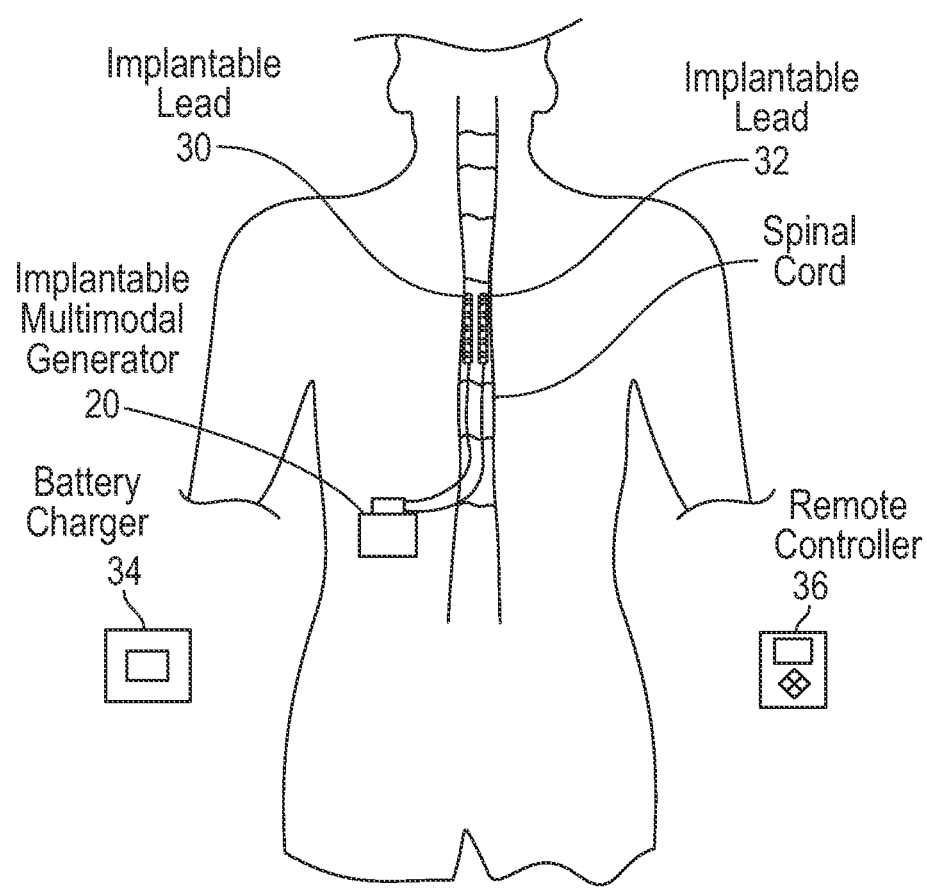
FIG. 13 illustrates conceptually the placement of an implantable system with a human subject in accordance with an embodiment of the present disclosure.

FIG. 13 illustrates conceptually another embodiment of an implantable system with a human subject in prone position. Shown is an example of an implantable system in which both leads 30 and 32 are positioned above the dorsal spinal cord at a particular vertebral level. A programmable implantable multimodal generator (IMG) 20 is attached to the leads using conductive cables and is powered by a rechargeable or non-rechargeable long-life battery contained within the Power Source module 21, within the implantable multimodal generator 20. An external battery charger 34 may be used for recharging of the generator using inductive, i.e., wireless, charging. A wireless remote control 36, which may be implemented with any number of wireless communication protocols, including Bluetooth or others, may be used to communicate with IMG 20 to enable a patient's adjustment of parameters at the discretion of the physician. The system may be programmed using an external programmer unit, such as a computer (not shown) that can transmit information to the IMG 20 via wireless communication protocols.

FIG. 14 illustrates conceptually another embodiment of an implantable system with a human subject in prone position. Shown is an example of an implantable system, similar to that illustrated with reference to FIG. 13 herein, in which leads are positioned in the neighborhood of a peripheral nerve.

According to still another aspect of the disclosure, a method for managing pain in a subject comprises activating glial cells by multimodal electromagnetic stimulation regulating any of genes for calcium binding proteins, cytokines, cell adhesion or specific immune response proteins, and administering a pharmacological substance to the subject systemically, epidurally, or intrathecally during a time period. In other embodiments, such a pharmacological substance may be injected through the stimulation lead, which may have a port to deliver the pharmacological agent directly into the epidural or intrathecal space. Optionally, the pharmacological agent may be impregnated onto the stimulation lead using a slow release formulation in order to provide a slow elution of the pharmacological substance into the neural tissue around the lead.

A pharmacological substance suitable for use with the disclosed method may comprise a metabotropic or ionotropic glutamate receptor antagonist such as (S)-4-carboxyphenylglycine (CPG), (RS)-a-methyl-4-carboxyphenylglycine (MCPG), or kynurenic acid (KYA). In another embodiment, a suitable pharmacological substance may comprise a potassium channel antagonist, such as 4-aminopyridine (4AP), or an alpha-2 adrenergic receptor agonist, such as clonidine, or a calcium channel agonist such as the w-conotoxin MVllC, a NMDA receptor agonist such as ketamine or glial cell modulators like alendronate, cyclosporine A, cannabinoid receptor agonist (CB1R or CB2R) or monoclonal antibodies against at least cytokines such as tumor necrosis factor alpha, Interleukin 1 or 6, etc., or fusion proteins like etanercept, or abatacept. Such pharmacological substances can help to activate or deactivate glial cells by modulating the release of glutamate, potassium or calcium ions in or out the glial cell.

In one embodiment, activating the glial cells comprises exposing the glial cells to a stimulus, which is a composite electromagnetic field. The multimodal signal resulting from a single, dual or multiple simultaneously applied electromagnetic fields may promote targeted delivery of the administered pharmacological agents by decreasing their resistance to penetrate tissue, while providing an electrical force that steers the pharmacological compounds towards the target neural tissue according to the electric properties (polarity, polarizability) of such pharmacological agent (iontophoretic effect). The stimulation characteristics of the priming component of the multimodal signal may decrease the tissue resistance so the pharmacological substance may penetrate better into the target neural tissue. Additionally, the polarity of the multimodal electric fields may be optimized to steer the pharmacological substance to the aforementioned target neural tissue.

Example 1

Figure 15:
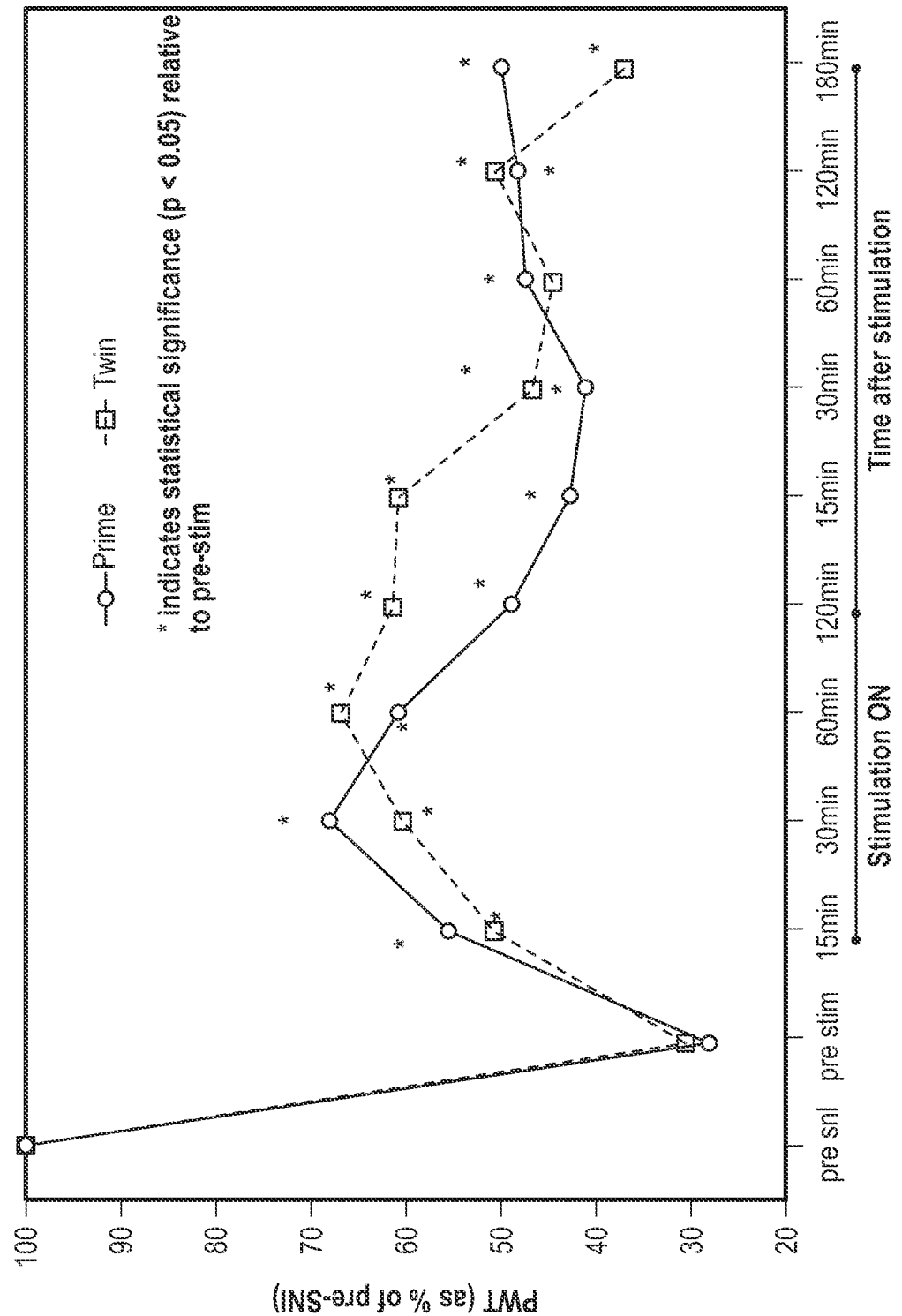
FIG. 15 illustrates conceptually a graph of results achieved in a pre-clinical animal study utilizing systems and methods in accordance with the present disclosure.

Referring to FIG. 15, an initial pilot study using an animal model for neuropathic chronic pain was carried out (n=29). In this study, a peripheral nerve injury was surgically induced by transecting the tibial and peroneal branches of the sciatic nerve at the point of trifurcation while sparing the sural nerve (spared nerve injury, SNI, model). After four days of transection, the subject develops mechanical and thermal hypersensitivity (allodynia), which is considered pain-like behavior. Subjects were implanted with a small cylindrical four-contact lead fitted surgically into their epidural space at the vertebral level corresponding to the innervation of the sciatic nerve. At day four post-surgery subjects were behaviorally tested using von Frey filaments. These filaments of different tensile strength are used to measure the sensitivity of a skin area affected by the nerve injury to mechanical stimulation. In the SNI model, the plantar area of the hind paw ipsilateral to injury becomes hypersensitive. A hypersensitive subject will withdraw its paw upon stimulation with a filament of very low tensile strength. Mechanical hypersensitivity was evident in the ipsilateral hind paw in comparison to the contralateral one, which was used as a normal behavior control.

In a particular example of multimodal stimulation, electrodes implanted in the epidural space of the rat above the dorsal aspect of the spinal cord were connected to a current source delivering a priming signal that consisted of a charge-balanced biphasic symmetric rectangular pulse oscillating at 1,200 Hz and a PW of 30 µs at an amplitude of 0.1 mA (33% motor threshold, MT). The was combined with a tonic signal which was a charged balanced biphasic symmetric rectangular pulse oscillating at 50 Hz, PW of 50 µs and amplitude of 0.2 mA (66% MT). Electrical stimulation was continuously applied for two hours and behavioral testing for mechanical sensitivity was performed every fifteen minutes while the subject was being stimulated. Behavioral testing was continued every fifteen minutes after stimulation was turned off for one hour and then every hour until three hours post stimulation. FIG. 16 shows the results as an average of the various recordings obtained from Behavioral data indicates that multimodal stimulation improves mechanical allodynia after fifteen minutes of stimulation with the improvement lasting for more than one hour after the stimulation is turned off, indicating that there is a residual effect of the applied fields, which suggest modulation of the nervous system.

Example 2

In the example, the genome-wide expression effects in ipsilateral dorsal spinal cord (DC) tissues of spinal cord stimulation (administered for 72 h) were assessed in rats induced with chronic neuropathic pain after peripheral nerve injury. Specifically, in the example genome-wide expression levels were compared between animals of one the most commonly used rodent models for chronic neuropathic pain (spare nerve injury, SNI) upon continuous SCS and sham-treated animals, i.e., animals in which the pain model was induced, and were implanted, but not stimulated.

The genome-wide expression profiling microarray commercially available for the laboratory rat employed in the current studies was capable of surveying the expression of about 21,000 genes. Enrichment analysis based on clustering statistics (using weighted gene correlation network analysis (WGCNA)) allowed for the identification of modules (or subsets) that contained genes that were highly correlated to each other in terms of biological role. Gene ontology analysis allowed for the grouping of genes within a module in terms of more specific biological processes and molecular functionality. Further refinement allowed for the identification of key genes within a particular pathway.

It was found by comparison of the genome of the treated animals that SCS upregulated and down-regulated genes associated with various interrelated processes, as described herein.

Comparative Genomics at the Spinal Cord

Because stimulation was performed atop the dorsal region of the spinal cord, cells of the dorsal spinal cord were examined for expression differences that would indicate the role of genes on molecular functionality and biological functions in this tissue. WGCNA identified that SCS significantly upregulated genes involved in activation of the immune system (false discovery rate (FDR) adjusted P-value=0.016); while genes involved in phosphorylation and activities related to transmembrane transport (FDR P-value=0.011) were down-regulated, as were genes associated with regulation of neuronal activity including regeneration and development. Refinement of the data identified 52 key genes. Among these, the following were identified as particularly noteworthy, since they have been described as involved in the processes of glial activation, immune response and neuronal activity:

Calcium binding protein (Cabp1): This gene was identified as significantly down-regulated (i.e., reduced by 1.4-fold to 1.5-fold) by SCS. The encoded Calcium-binding protein 1 regulates calcium-dependent activity of inositol 1,4,5-triphosphate (ITP) receptors. ITP receptors are involved in the signaling between astrocytes via calcium waves, which have been posited to play a key role in the intercellular communication that propagates astrocyte activation. Down regulation of Cabp1 likely diminishes the activation of astrocytes that is otherwise conducive to the synaptic reshaping that results in a chronic pain state.

Toll-like receptor 2 (Tlr2): This gene was identified as significantly upregulated (i.e., increased by 2.4-fold to 2.8-fold) by SCS. Tlr2 is expressed in activated glial cells, including microglia and astrocytes; however, expression in activated microglia is larger than expression in astrocytes. The encoded Toll-like receptor 2 protein induces a cascade of events that likely leads to the secretion of anti-inflammatory cytokines, such as IL-10.

Chemokine Cxcl16: This gene was identified as significantly upregulated (i.e., increased by 2.2-fold to 3.6-fold) by SCS. This is a transmembrane chemokine which drives the interplay between glial cells and neurons as a result of stimulus. Cxcl16 is expressed by microglia and astrocytes as a neuroprotective agent. Up-regulation of this gene by SCS is indicative of a neuroprotective process in the spinal cord likely involving the modulation of microglia.

Glial maturation factor (Gmfg): This gene was identified as significantly upregulated (i.e., increased by 2.1-fold to 2.3-fold) by SCS. This gene has been thought to be involved in glial differentiation and neural regeneration. There is not much known about this gene. Its upregulation by SCS may be associated with glial activation processes that may lead to neuronal regeneration.

Other key genes identified as upregulated or down-regulated by spinal cord stimulation are described with reference to Table 1-1 below:

TABLE 1-1

| Process | Gene | Description | Notes |
|---|---|---|---|
| Selected Genes up-regulated by SCS | | | |
| Inflammation and Immune Response | Ly86 | lymphocyte antigen 86 (2.5- fold to 2.6-fold) | Cooperate with toll like receptor to mediate the innate immune response |
| | Cd68 | Cd68 molecule (2.7-fold to 2.8-fold) | Phagocytic activities of tissue macrophages |
| | Apbb1ip | amyloid beta (A4) precursor protein (1.7-fold to 1.8-fold) | Signal transduction from Ras activation to actin cytoskeletal remodeling |
| | Casp1 | caspase 1 (1.8-fold to 1.9-fold) | Cleaves IL-1 beta |
| | Ifi30 | interferon gamma inducible (2.2-fold to 2.3-fold) | MHC class II-restricted antigen processing |
| | Cd53 | Cd53 molecule (2.2-fold to 2.3-fold) | Mediate regulation of cell development, activation, growth and motility |

TABLE 1-1-continued

| Process | Gene | Description | Notes |
|---|---|---|---|
| | Tnfaip8l2 | tumor necrosis factor, alpha-induced protein (2.2- fold to 2.3-fold) | Regulator of innate and adaptive immunity by maintaining immune homeostasis |
| | Il1b | interleukin 1 beta (3.7-fold to 3.8-fold) | Mediator of the inflammatory response. Induces cyclooxygenase-2 (COX2) to contribute to inflammatory pain. |
| | Cxcl17 | chemokine (C—X—C motif) ligand 17 (2.1-fold to 2.2-fold) | May be a chemokine regulating recruitment of monocytes and immature dendritic cells |
| | Itgb2 | integrin, beta 2 (1.9-fold to 2.0-fold) | Participate in cell adhesion as well as cell-surface mediated signaling |
| | Timp1 | TIMP metallopeptidase inhibitor 1 (2.9-fold to 3.0-fold) | Inhibitors of the matrix metalloproteinases, involved in degradation of the extracellular matrix |
| | Tnfsf12 | Tumor Necrosis Factor (Ligand) Superfamily (1.2-fold to 1.3-fold) | Cytokine that belongs to the tumor necrosis factor (TNF) ligand family. It can induce apoptosis via multiple pathways of cell death in a cell type-specific manner. |
| | Il2rg | Interleukin 2 Receptor, Gamma (1.3-fold to 1.4-fold) | Common subunit for the receptors for a variety of interleukins |
| Selected genes down-regulated by SCS | | | |
| Ion channel regulation | Wwp1 | WW domain containing E3 ubiquitin protein ligase 1 (1.3-fold to 1.4-old) | Ubiquitinates and promotes degradation of SMAD2 in response to TGF-beta signaling |
| | Micu3 | Mitochondrial calcium uptake family (1.4-fold to 1.5-fold) | Essential regulator of mitochondrial calcium uptake under basal conditions |
| | Grin2a | Glutamate receptor, ionotropic, N-methyl D-aspartate 2A (1.4-fold to 1.5-fold) | Receptor activation requires binding of glutamate and glycine, leads to an influx of calcium into postsynaptic region activating pathways. NMDA receptors have a critical role in excitatory synaptic transmission and plasticity in the CNS. |
| Binding and metabolic pathways | Amph | Amphiphysin (1.4-fold to 1.5-fold) | Associated with the cytoplasmic surface of synaptic vesicles |
| | Gabrg1 | Gamma-Aminobutyric Acid (GABA) A receptor, Gamma 1 (1.5-fold to 1.6-fold) | Protein encoded by this gene is an integral membrane protein and inhibits neurotransmission by binding to the benzodiazepine receptor and opening an integral chloride channel |
| | Gabra2 | Gamma-Aminobutyric Acid (GABA) A Receptor, Alpha 2 (1.4-fold to 1.5-fold) | |
| | Gria3 | Glutamate receptor, ionotropic, AMPA 3 (1.3-fold to 1.4-fold) | Receptor for glutamate, functions as ligand-gated ion channel in the CNS, plays an important role in excitatory synaptic transmission |
| Cell growth | Knca1 | Potassium Voltage-Gated Channel, Shaker-Related Subfamily (1.3-fold to 1.4-fold) | Mediates the voltage-dependent potassium ion permeability of excitable membranes |
| | Kifc3 | Kinesin Family Member C3 (1.2-fold to 1.3-fold) | Molecular motor that use ATP hydrolysis to translocate cargoes along microtubules |

TABLE 1-1-continued

| Process | Gene | Description | Notes |
| --- | --- | --- | --- |
| ATP related, transmembrane/ transporter activity | Igsf1 | Immunoglobulin Superfamily (1.9-fold to 2.0-fold) | Thought to participate in the regulation of interactions between cells |
| Cell regulation | Oprm1 | Opioid Receptor, Mu 1 (1.3-fold to 1.4-fold) | Principal target of endogenous opioid peptides and opioid analgesic agents such as beta-endorphin and enkephalins. |

For the above-referenced genes, it is contemplated that expression level changes of any magnitude deemed statistically significant can be predictive of outcome (e.g., a biphasic signal can be manipulated for sufficient duration to produce a statistically significant change in the expression of one or more such genes within the modulated glial cells, as indicative of SCS having achieved a desired effect upon a subject). Statistically significant levels of up-regulation can include at least 1.2-fold, at least 1.3-fold, at least 1.4-fold, at least 1.5-fold, at least 1.6-fold, at least 1.7-fold, at least 1.8-fold, at least 1-9-fold, at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, at least 3.1-fold, at least 3.2-fold, at least 3.3-fold, at least 3.4-fold, at least 3.5-fold, at least 3.6-fold, at least 3.7-fold, at least 3.8-fold, at least 3.9-fold, at least 4-fold, at least 5-fold, etc. in an assayed cell, population and/or tissue(s), as compared to an appropriate control (e.g., control cell(s), tissue and/or value). Similarly, statistically significant levels of down-regulation can include at least 1.2-fold, at least 1.3-fold, at least 1.4-fold, at least 1.5-fold, at least 1.6-fold, at least 1.7-fold, at least 1.8-fold, at least 1-9-fold, at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, at least 3.1-fold, at least 3.2-fold, at least 3.3-fold, at least 3.4-fold, at least 3.5-fold, at least 3.6-fold, at least 3.7-fold, at least 3.8-fold, at least 3.9-fold, at least 4-fold, at least 5-fold, etc. in an assayed cell, population and/or tissue(s), as compared to an appropriate control (e.g., control cell(s), tissue and/or value).

Many of the genes involved in the inflammatory and immune response are associated with glial activity. Peripheral nerve injury is accompanied by regulation of genes and proteins not only at the site of injury, but also in the afferent ipsilateral CNS structures such as the DRG and the spinal cord. Proteomic analysis was recently performed in the spinal cord and DRG of the SNI animal model for neuropathic pain. This study indicated that transport and translocation of proteins was observed along the axon towards the soma, and then reciprocal protein transport back to the periphery to induce axon regeneration. Interestingly, the spinal cord presented with neuroprotective proteins, some associated with glial cell activation. The activation of glial cells following injury induced a cascade of events including an inflammatory and immune response, which then developed into peripheral sensitization that was conducive to ectopic firing of neurons. The alarm eventually extended to the CNS at the level of the spinal cord, where the microglia apparently attempted to protect the integrity of the system. Eventually, glial cells overreacted and induced the release of factors that reshaped the synapses. These changes in the synaptic plasticity manifested as chronic pain.

The results indicate that electrical stimulation of the spinal cord elicited regulation of genes and proteins that modulate the interactions between glial cells and neurons. It is plausible that these molecular events produce analgesia.

Example 3

The effect of phase polarity upon the modulation of genes previously presented was carried out using an animal model of chronic neuropathic pain. In this example, tissues from the spinal cord were obtained from animals, which were stimulated using a rectangular waveform at a frequency of 50 Hz and a pulse width of 200 μs per phase which were either monophasic cathodic, monophasic anodic, or symmetric biphasic with an initial cathodic polarity. RNA from tissues was extracted and cDNA was prepared by reverse transcription. RNA expression levels were assessed using real-time PCR, with levels quantified and standardized. Based on the above experiments (example 2), a panel of genes including markers for glial activation (tlr2, cxcl16), calcium-dependent glial processes (Cabp1), immune system activation (cd68), and an opioid receptor (oprm1) was selected for analysis.

FIGS. 17A-17E illustrate conceptually graphs of observed expression levels of selected genes relative to the polarity of the phase used in the stimulation waveform, including a) Calcium binding protein (Cabp1); b) Chemokine (Cxcl16); c) Toll-like receptor 2 (Tlr2); d) Cd68 molecule; and e) Opioid receptor mu-1 (Oprm1). It was evident that the polarity of the signal phase influenced regulation of these genes. Biphasic stimulation increased the levels of genes associated with glial activation (Tlr2 and Cxcl16) relative to anodic and cathodic stimulation in response to the release of glutamate from astrocytes. Biphasic stimulation increased the levels of Cabp1 relative to monophasic stimulation (cathodic or anodic). Monophasic stimulation (cathodic or anodic) and biphasic stimulation both produced similar levels of the immune-related gene Cd68, as well as the gene encoding for the opioid receptor, Oprm1.

Example 4

The subject patient was a 65 y/o female patient with diagnosis of Diabetic Neuropathy Syndrome complaining of severe bilateral pain in the lower extremities all the way to the feet. Patient had failed multiple medical treatments including physical therapy, medication management and surgical intervention.

The patient underwent a spinal cord stimulator trial with a high frequency paresthesia-free based SCS system. Two leads were positioned in the posterior epidural space with the tip of one of the leads located at the top of T8 and the other at the tip of T9. Patient returned seven days later for conclusion of the trial with high frequency paresthesia-free SCS, the patient reported only 30% pain relief.

At this point, the multimodal stimulation system of the present disclosure was applied. The system was reprogrammed using two external generators to generate a composite signal in the neural tissue. One generator was set for tonic at 50 Hz, 400 µs PW. The other was set for priming at either 900 or 1,200 Hz, 150 µs PW. The amplitude of the 50 Hz signal was initially set at 0.6 mA and the amplitude of the 900 Hz signal was initially set at 2.2 mA before the patient went home. These amplitudes did not induce paresthesia during treatment. Patient reported 57% pain relief in the legs after 20 hours of therapy.

Patient was reprogrammed to receive a priming frequency of 1,200 Hz. After reprogramming, patient continued experiencing pain relief without tingling. More important, pain relief was increased to 71% after 54 hours of reprogramming.

In Summary of Trial:
1. Subject patient did not experience paresthesia during the four days of treatment.
2. Patient reported that the paresthesia-free Multimodal treatment was superior to high frequency stimulation treatment.
3. Patient reported 71% of pain relief in her legs and feet.
4. Sharp pain in legs was significantly reduced.
5. Burning sensation in the feet was alleviated which allowed patients to endure longer walks than before therapy.

Example 5

The subject patient was a 76 y/o female diagnosed with failed back surgery syndrome. Patient has suffered from chronic pain in the lower back and legs. Subject has been treated with conventional treatments without clinical success. Pain numerical rate score before treatment was reported as 8, with pain in the back radiating to the legs. A pair of SCS trial leads were implanted using a non-parallel alignment (i.e., they were offset from each other), and a high frequency paresthesia-free program had been set. Patient reported total pain relief in the back and legs leg from the high frequency treatment. Patient reported improvement in sleep and a decrease of Vicodin ingestion. Patient was then reprogrammed using multimodal stimulation with priming parameters set at 1,200 Hz, 150 µs PW and 3 mA, while tonic parameters were set at 50 Hz, 400 µs PW and 4.9 mA.

Patient experience very little pain (0-1 in a 0-10 numerical rating scale) in back and legs during the following days under multimodal therapy.

Patient reported also that she was able to increase her activity and could climb up and down stairs (an activity she avoided before SCS treatment). Family was impressed with improvements in daily activity since being under therapy trial period.

In Summary:
1. Patient did not experience paresthesia during three days multimodal SCS therapy.
2. Patient was able to reduce pain medication ingestion.
3. Patient reported minimal back pain and leg pain (mean of 0.5 in the 0-10 numerical scale).
4. Patient reported significant improvement on sleep habits.
5. Patient reported significant increase in her ability to carry out daily activities that she could not do before SCS therapy.

Example 6

Figure 16A:
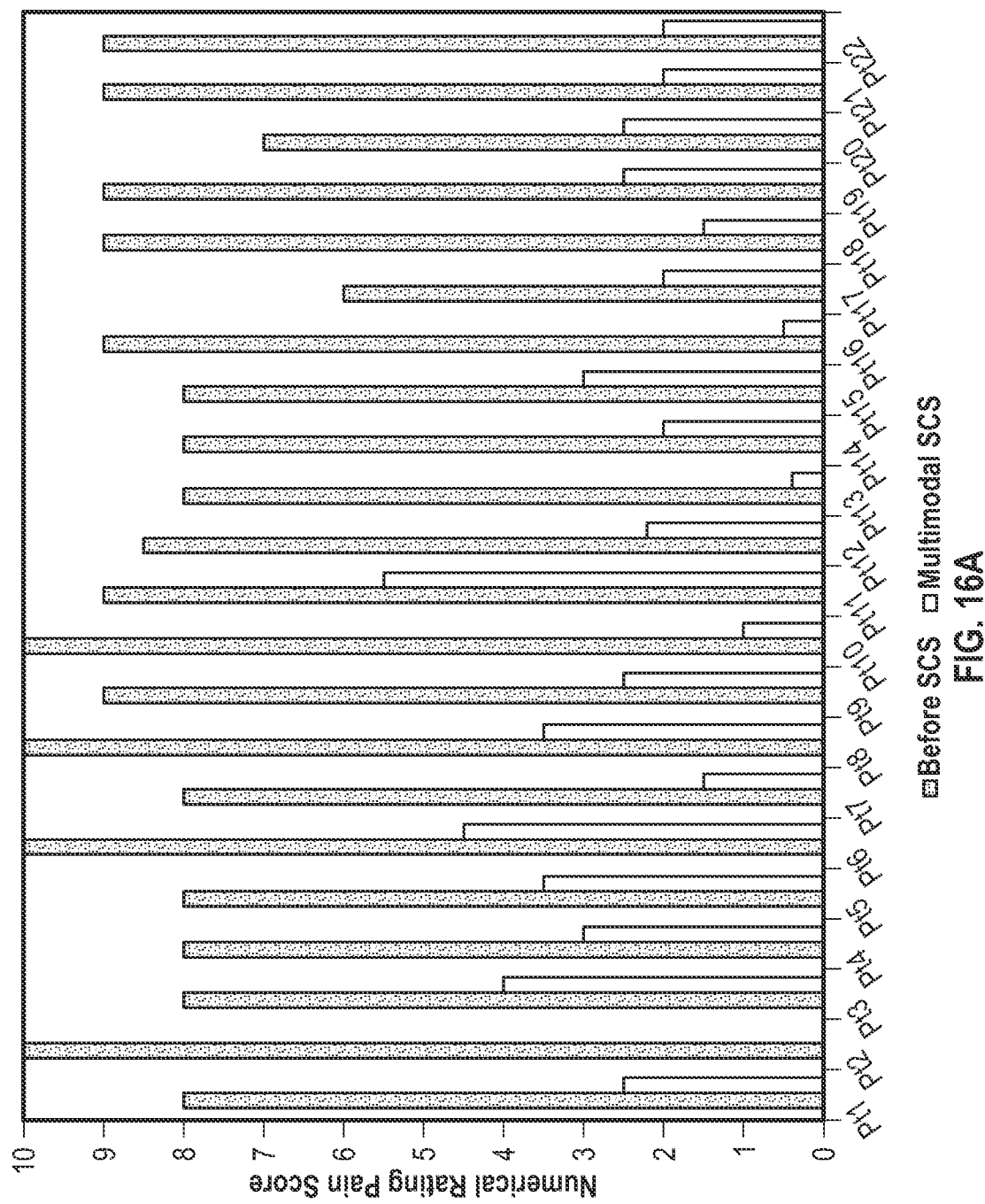
FIGS. 16A and 16B illustrate conceptually graphs of results achieved in a short time pilot clinical trial period utilizing systems and methods in accordance with the present disclosure.
Figure 16B:
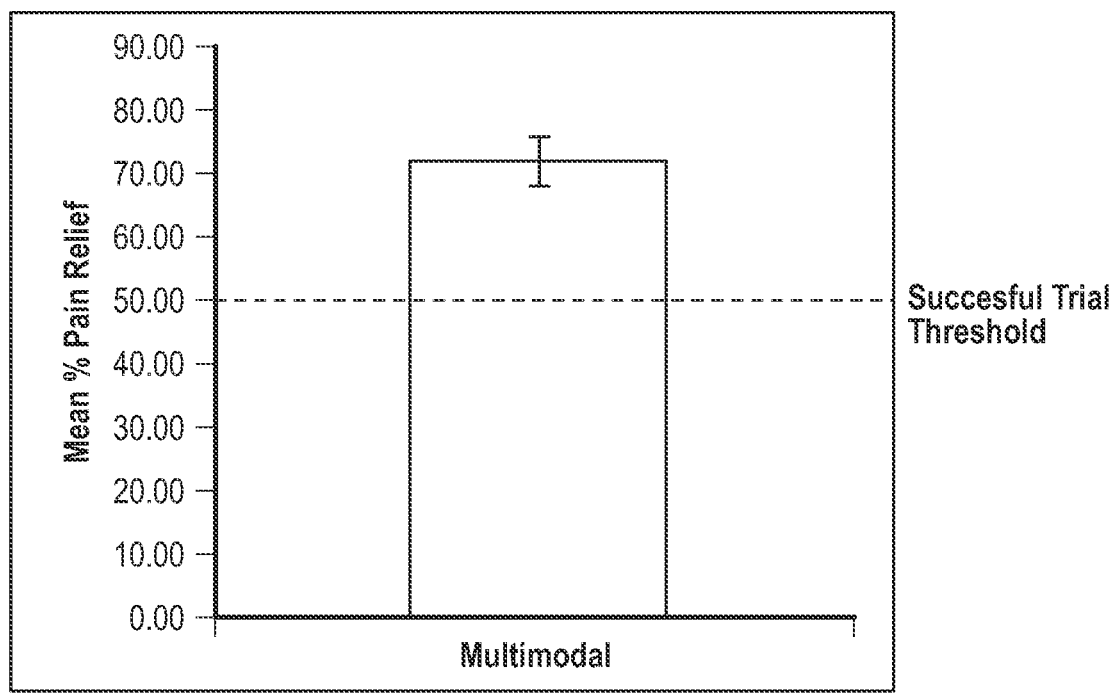
Figure 17A:
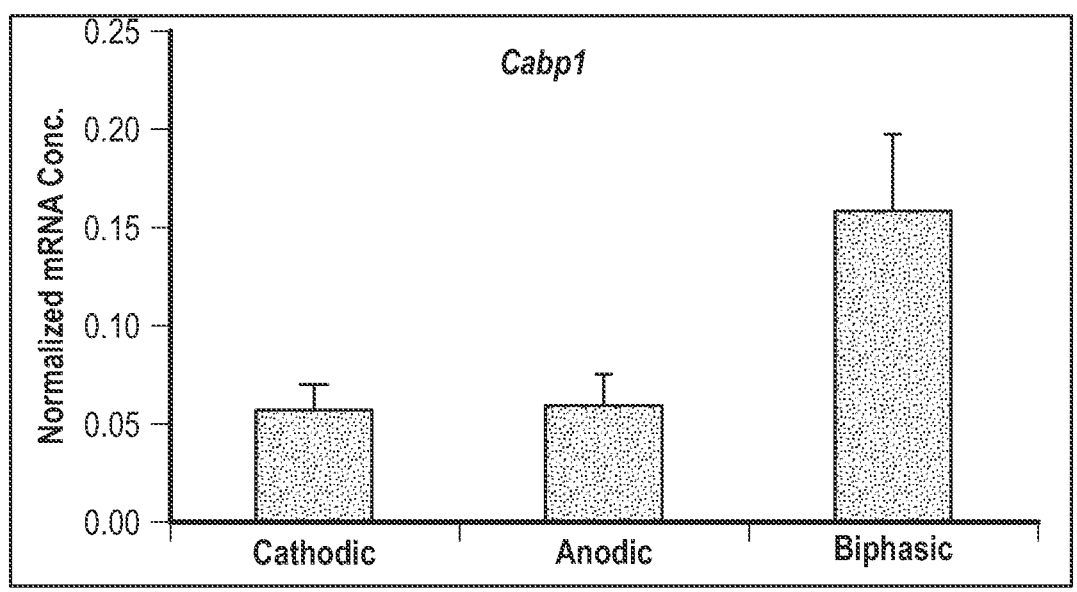
Figure 17B:
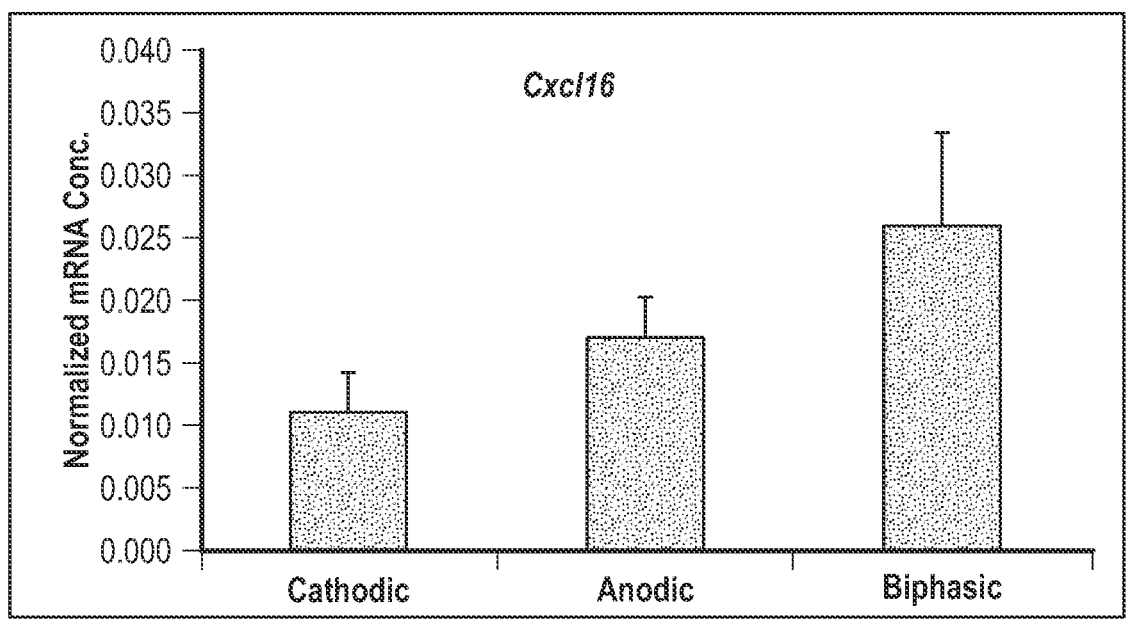
Figure 17C:
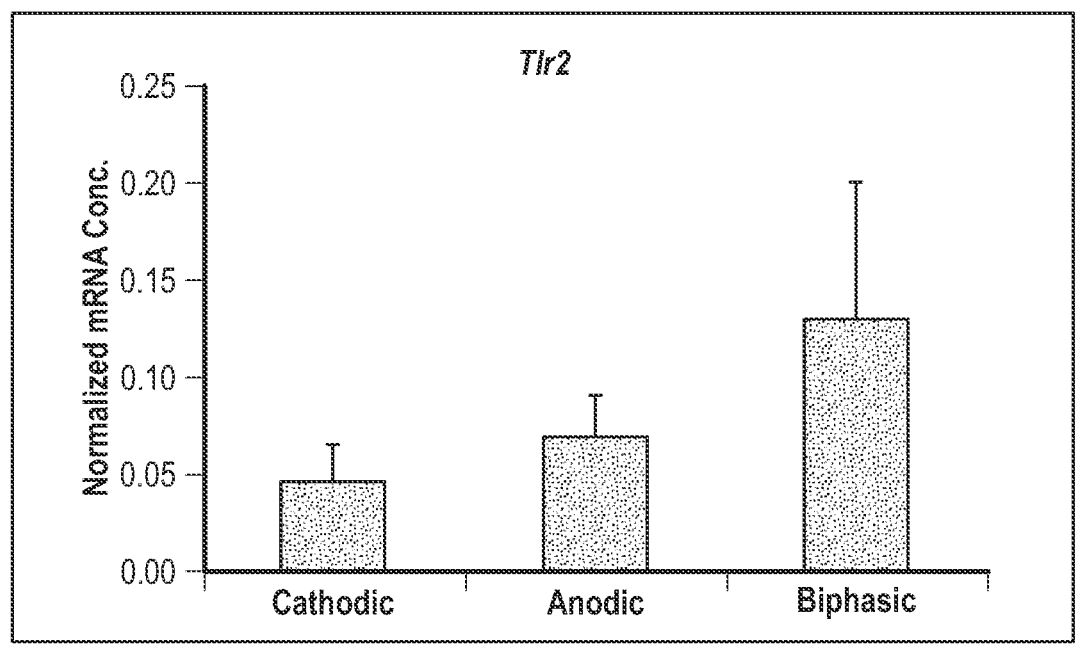
Figure 17D:
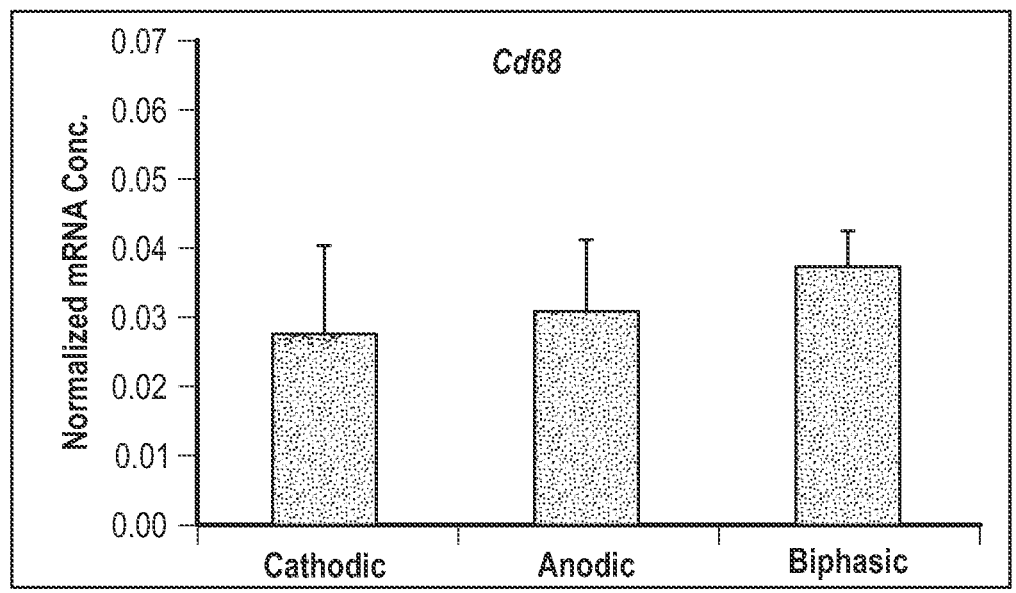
Figure 17E:
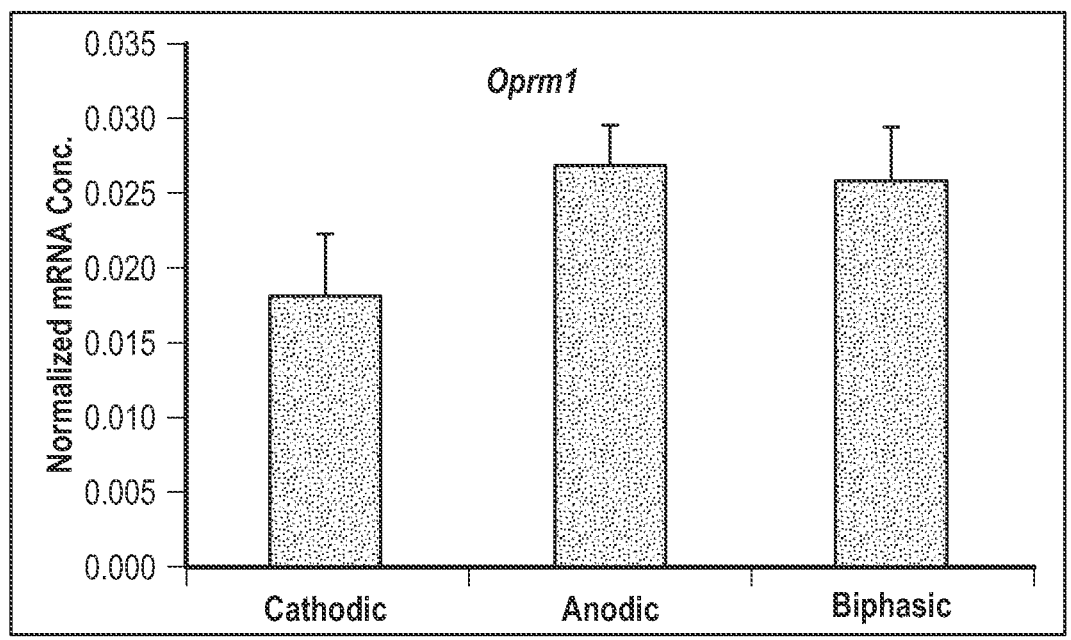

Referring to FIGS. 16A and 16B, an observational study using human volunteers was carried out (n=22). These subjects were part of a trial period for commercial spinal cord stimulation systems administered under standard clinical practice. Subjects voluntarily accepted to try multimodal modulation after they had completed their trial period. Success in a trial period is indicated by pain relief equal or above 50% relative to the pain numerical rating score (NRS) present before the spinal cord stimulation therapy was commenced. All subjects had been implanted with two eight-electrode trial leads. Thirteen of them had leads staggered relative to each other and five of them had leads parallel to each other. Nine of the subjects had trialed conventional paresthesia-based stimulation systems (50-70 Hz) and thirteen of them had trialed a high frequency system (10,000 Hz). Four of the subjects failed the trial with conventional paresthesia-based stimulation (50-70 Hz) and three the high frequency paresthesia-free stimulation (10,000 Hz). Multimodal stimulation was tried for as short as three hours and for as long as four days. All but one of the 22 subjects successfully tried multimodal stimulation under the paresthesia or perception threshold (PT). The mean pain relief of the subjects was 72% and all subjects declared to be satisfied with multimodal stimulation therapy.

Exemplary embodiments describe a variety of patient fitting/setup options. With reference to FIG. 18, a workflow for fitting/setting up a patient is shown generally at 1800, and includes placing an electrode or electrode group at a nerve area (spinal nerves, peripheral nerves, specific areas or clusters, etc.), shown in step 1802. For an electrode or electrode group placed at the nerve area, a signal (which includes a frequency and pulse width), is ramped up in intensity/amplitude until paresthesia is indicated (step 1804). Once paresthesia is indicated, the Intensity is either ramped up or down to the point that paresthesia is no longer indicated. This provides an indication of a paresthesia threshold, which may be stored as a paresthesia threshold. Optionally, a reduction of the intensity/amplitude of the signal may be performed at 1810. At 1812, an adjustment of intensity/amplitude is performed (e.g., incrementally over time) until an optimal or preferred setting is established for a patient.

In exemplary embodiments, in post-operation, a patient program may be set to one of a range of percentages of perception (% TPT or % PPT). In one exemplary embodiment, such range is from 65%-75% perception. Other exemplary embodiments contemplate ranges between 20% and 90%, 30% and 80%, 40% and 80%, 50% and 80%, 60% and 80%, among others. Additionally, % TPT and % PPT may vary, with different percentages between different frequency types or different percentages between electrodes or groups of electrodes according to different positioning or different effect.

In exemplary embodiments, intensity/amplitude of the signals may initially be set to zero, with subsequent increase until the patient indicates the perception threshold, with subsequent reduction to the above-mentioned percentage of PT. Further, in exemplary embodiments, program settings for each electrode or group of electrodes are individually adjustable.

Additionally, in exemplary embodiments, the efficiency of programming can be increased by performing a setup for one pulse on a group of electrodes, followed by copying the program settings (matching settings) or by making certain changes to the program settings (varying settings) before pasting those program settings into other groups of electrodes.

In exemplary embodiments, establishment of perception (TPT or PPT) may also be done separately for each group of electrodes, thereby providing a relevant level for determining the effective level for each of different desired effects (priming and tonic, positional, etc.) or providing a baseline tailored to a specific patient, which can be used to quickly find an optimal or preferred setting for that patient.

Further, reduction of amplitude to a percentage or perception (TPT or PPT), followed by increasing each of groups of electrodes or types of groups (priming vs. stimulation/tonic) can be beneficial because: it can facilitate a beneficial selection from both a pain reduction and power consumption perspective (versus starting at perception and decrementing, which is also considered by the present specification); it recognizes that even though there is a synergy between the different stimulation types (priming and tonic), the combination is additionally effective when amplitudes for each group or type are set independently; and it recognizes that the different stimulation types may be differently felt by the patient, with the patient preferring one over the other.

As has been noted, additional exemplary embodiments include alternate methods for establishing a comfort level for a patient, such as establishing perception and, rather than reducing to a percentage, incrementing up or down to find a comfort level. As before, this may be done for one or more groups and replicated (or replicated in part) or may be done individually without such replication.

A description of an exemplary programming setup procedure, with an exemplary increase in programming efficiency, follows.

Example 7

A certain spinal location is selected for assignment of electrodes. For example, an electrode nearest to the middle of T8 and T9 may be designated. For a "Group A", Program 1, the cathode is placed on/assigned to the electrode nearest to the middle of T8. An anode is placed two electrodes below the cathode. The device rate is set to a desired frequency, e.g., 300 Hz; and the program rate is changed to a lower rate than the device rate, e.g., ⅙ device rate, or 50 Hz. Pulse width may be set to a desired width, e.g., 200 microseconds. Program 1 may be closed. For a Program 2 in Group A, the cathode may be placed on the electrode nearest to the middle of T9, with the anode placed two electrodes below the cathode. Some variation of pulse width may be set, e.g., PW=170 microseconds. Program 2 may be closed.

In an exemplary program setup, Group B may be set up the same as for Group A, except for being ½ vertebral segment lower than Group A (and on a second lead). Group B is activated and program 1 selected. Program 1 is activated, with all electrodes selected. The cathode and anode is then slid down one half a vertebral segment lower (with the cathode now on the electrode nearest the top of T9). Program 2 is activated, all electrodes selected; and cathode and anode are slid down one half a vertebral segment lower (with the cathode on the electrode nearest to the T9/T10 disc space. The program is closed.

In a further exemplary "Group C" program setup, the electrode setup is the same as for Group A, except that it is one quarter of a vertebral segment lower than for Group A, again, on the second lead. Group C is activated, selecting program 1. Program 1 is activated, selecting all electrodes. Subsequently, the cathode and anode are slide one quarter of a vertebral segment lower (with the cathode being on the electrode nearest the bottom of T8). Subsequently, Program 2 is activated, with all electrodes selected, the cathode and anode being moved one quarter of a vertebral segment lower (with the cathode on the electrode nearest the bottom of T9). The program is closed.

In exemplary embodiments, for programming amplitudes, for Group A, Program 1 (A1), the intensity in Program 1 is ramped up until paresthesia is felt. Subsequently, it is ramped down in individual increments until the patient loses paresthesia. This is recorded as the LD paresthesia threshold. Intensity is subsequently decreased to a percentage of PT (e.g., 70%) as a final LD amplitude, with stimulation remaining on for Program 1.

Changing to Program 2 in Group A (A2), intensity in Program 2 is ramped up until paresthesia is felt. Subsequently, intensity is ramped down in individual increments until the patient loses paresthesia. The value is recorded as the HD paresthesia threshold. Intensity is decreased to a percentage of PT (e.g., 65%) and recorded as a final HD amplitude. Stimulation for Program 2 is kept on.

For Group A, Program 3 (A3), intensity is increased to that of Group A, Program 2. For Group A, Program 4 (A4), intensity is increased to that of Group A, program 2.

In exemplary embodiments, for programming amplitudes, for Group B, Program 1 (B1), the intensity in Program 1 is ramped up until paresthesia is felt. Subsequently, it is ramped down in individual increments until the patient loses paresthesia. This is recorded as the LD paresthesia threshold. Intensity is subsequently decreased to a percentage of PT (e.g., 70%) as a final LD amplitude, with stimulation remaining on for Program 1.

Changing to Program 2 in Group B (B2), intensity in Program 2 is ramped up until paresthesia is felt. Subsequently, intensity is ramped down in individual increments until the patient loses paresthesia. The value is recorded as the HD paresthesia threshold. Intensity is decreased to a percentage of PT (e.g., 65%) and recorded as a final HD amplitude. Stimulation for Program 2 is kept on.

For Group B, Program 3 (B3), intensity is increased to that of Group B, Program 2. For Group B, Program 4 (B4), intensity is increased to that of Group B, program 2.

In exemplary embodiments, for programming amplitudes, for Group C, Program 1 (C1), the intensity in Program 1 is ramped up until paresthesia is felt. Subsequently, it is ramped down in individual increments until the patient loses paresthesia. This is recorded as the LD paresthesia threshold. Intensity is subsequently decreased to a percentage of PT (e.g., 70%) as a final LD amplitude, with stimulation remaining on for Program 1.

Changing to Program 2 in Group C (C2), intensity in Program 2 is ramped up until paresthesia is felt. Subsequently, intensity is ramped down in individual increments until the patient loses paresthesia. The value is recorded as the HD paresthesia threshold. Intensity is decreased to a percentage of PT (e.g., 65%) and recorded as a final HD amplitude. Stimulation for Program 2 is kept on.

For Group C, Program 3 (C3), intensity is increased to that of Group C, Program 2. For Group C, Program 4 (C4), intensity is increased to that of Group C, program 2.

In exemplary program setup, the program for A2 is copied and pasted into A3 and A4. Similarly, the program for B2 is copied and pasted into B3 and B4. Finally, the program for C2 is copied and pasted into C3 and C4. Accordingly, in this exemplary embodiment, there are 4 programs in each group, with 3 groups created, all with 0.0 mA.

In exemplary embodiments, subsequent to initial setup, a patient may adjust frequency up towards PT in spaced apart increments, e.g., with 4 hours wait time in between adjustments to facilitate accurate assessment of improvement in pain relief. Exemplary embodiments record and/or regulate such adjustments, wait times and assessments. In further exemplary embodiments, objective feedback from patients may be incorporated into such adjustment considerations, for example using informed cycling via sensing changes in posture of the patient or other physically sensed patient aspects, conditions or parameters.

The reader will appreciate that the multimodal modulation techniques described herein, achieved with a composite signal, e.g., frequency, amplitude, or pulse width modulated, and multi-modal modulation, can be utilized for regulation of genes and proteins that modulate the interactions between glial cells and neurons as described herein.

As used herein, the term "pharmacological substance" means any tangible chemical, drug, medicine or therapeutic substance, either synthetic or naturally occurring, regardless of the form of administration to the subject, that is administered to the body of the subject.

At various places in the present specification, values are disclosed in groups or in ranges. It is specifically intended that the description includes each and every individual sub-combination of the members of such groups and ranges and any combination of the various endpoints of such groups or ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

For purposes of clarity and a concise description, features are described herein as part of the same or separate embodiments, however, it will be appreciated that scope of the concepts may include embodiments having combinations of all or some of the features described herein.

It will be obvious to those recently skilled in the art that modifications to the apparatus and process disclosed here in may occur, including substitution of various component values or nodes of connection, without parting from the true spirit and scope of the disclosure as defined by the claims set forth herein. For example, although the embodiments described herein disclose primarily the use of pulsed rectangular signals, other waveform shapes may be similarly used to obtain the same effects. For example, any of a monophasic pulse wave, charge balanced biphasic pulse wave, charge imbalanced biphasic pulse wave, charge balanced biphasic with delay pulse wave, charge balanced biphasic fast reversal wave, and charge balanced biphasic slow reversal wave may be utilized as stimulating waveforms in the multimodal modulation techniques described herein. In addition, other varying electromagnetic fields defined by periodic electric signals having different waveform shapes may be used as well as noise signals and even non-periodic electric signals having irregular nonrepeating shapes.

What is claimed is:

1. A method for managing pain in a subject comprising:
    applying via at least one electrode a first phase segment of a biphasic signal to a nerve area, the first phase segment having a frequency of between 750 Hz and 1400 Hz; and
    applying via said at least one electrode a second phase segment of the biphasic signal to said nerve area, the second phase segment having a frequency lower than that of the first phase segment.

2. The method of claim 1 wherein first phase segment has a frequency of about 1200 Hz (burst) and 900 Hz (average).

3. The method of claim 1 wherein the second phase segment has a frequency of about 50 Hz.

4. The method of claim 1 wherein the first phase segment and the second phase segment have any of different respective amplitudes, waveform shapes, widths, phase polarities, and phases relative to each other.

5. The method of claim 1 wherein the biphasic signal is an asymmetric biphasic signal.

6. The method of claim 1 wherein the biphasic signal is a frequency modulated signal.

7. The method of claim 1 wherein the biphasic signal is a phase modulated signal.

8. The method of claim 1 wherein the biphasic signal is a pulse width modulated signal.

9. The method of claim 1 wherein application of biphasic signal is performed without the administration of a pharmacological substance to the subject.

10. The method of claim 1 wherein the pulse width of the first phase segment is between about 170 and 400 microseconds.

11. The method of claim 1, wherein the biphasic signal is derived from a first electric signal having a current amplitude set to a value corresponding to a percentage of perception threshold of the subject.

12. The method of claim 11, wherein amplitude of the signals are initially set to zero, with subsequent increase until the patient indicates a perception threshold, with subsequent reduction to a predetermined percentage of perception.

13. The method of claim 12, wherein the percentage perception is between 20% and 90%.

14. The method of claim 13, wherein the percentage of perception is between 65% and 75%.

15. The method of claim 11, further comprising generating a program for said biphasic signal as a first pulse on at least one electrode, and further comprising generating an exact or altered copy of said program for use on a separate electrode or group of electrodes.

16. The method of claim 11, further comprising generating a program for said biphasic signal as a first pulse on at least one electrode, and further comprising separately generating programs for at least one separate electrode or group of electrodes, including independently assessing perception for the patient and adjusting amplitude of the signal up or down therefrom.

17. The method of claim 1, wherein said nerve area comprises a spinal cord nerve area.

18. The method of claim 1, wherein said nerve area comprises a peripheral nerve area.

19. The method of claim 1, wherein said nerve area comprises a cluster of nerves.

20. The method of claim 1, wherein the first phase segment comprises a priming component.

21. The method of claim 20, wherein the second phase segment comprises a tonic component.

22. The method of claim 1, wherein the biphasic signal is derived from:
    a first electric signal having a current amplitude set to a value corresponding to a percentage of priming perception threshold (PPT) of the subject; and
    a second electric signal having a current amplitude set to a value corresponding to a percentage of tonic perception threshold (TPT).

* * * * *